United States Patent [19]

Cox et al.

[11] 4,419,352

[45] Dec. 6, 1983

[54] PYRANOQUINOLINONES AND ANALOGS THEREOF

[75] Inventors: David Cox; Hugh Cairns, both of Loughborough; Nigel Chadwick, West Bridford; John L. Suschitzky, Loughborough, all of England

[73] Assignee: Fisons Limited, London, England

[21] Appl. No.: 236,329

[22] Filed: Feb. 20, 1981

Related U.S. Application Data

[63] Continuation of Ser. No. 82,994, Oct. 9, 1979, abandoned.

[30] Foreign Application Priority Data

Oct. 31, 1978 [GB] United Kingdom ............... 42679/78
Jun. 14, 1979 [GB] United Kingdom ................. 7920760

[51] Int. Cl.³ ................. C07D 491/04; C07D 413/14; A61K 31/535; A61K 31/47
[52] U.S. Cl. .............................. 424/248.4; 424/248.5; 424/248.52; 424/248.53; 424/248.54; 424/248.56; 424/256; 544/126; 546/89; 546/92
[58] Field of Search .................... 546/89, 92; 424/256, 424/248.4, 248.5, 248.52, 248.53, 248.54, 248.56; 544/126

[56] References Cited

PUBLICATIONS

Chenmical Abstracts, Chemical Substance Index O–P, Part 4 of 5 Parts), p. 5928 CS, Dec. 31, 1981.

*Primary Examiner*—Alan L. Rotman
*Attorney, Agent, or Firm*—Merriam, Marshall & Bicknell

[57] ABSTRACT

There are described compounds of formula I,

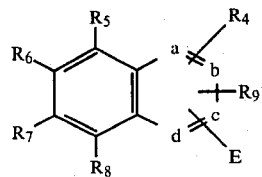

in which
an adjacent pair of $R_5$, $R_6$, $R_7$ and $R_8$ form a chain $-CZC(G_1)=(G_2)-Z-$,
$R_4$, $R_9$ and the remainder of $R_5$, $R_6$, $R_7$ and $R_8$, which may be the same or different, each represent hydrogen, alkyl, halogen, alkenyl, $-NO_2$, $-NR_1R_2$, $-OR_3$, $-S(O)_nR_3$; or alkyl substituted by hydroxy, amino, alkoxy or carbonyl oxygen,
n is 0, 1 or 2,
$R_1$ and $R_2$, which may be the same or different, each represent hydrogen, alkyl, $-CONHR_3$, phenyl or phenyl substituted by alkyl or halogen, or $R_1$ and $R_2$ together with the nitrogen atom to which they are attached form a 5 or 6 membered heterocyclic ring,
$R_3$ represents hydrogen, alkyl, alkenyl or phenyl,
one of $G_1$ and $G_2$ is hydrogen and the other is a group E,
each E, which may be the same or different, is $-COOH$, a 5-tetrazolyl group, or a carboxamidotetrazole group,
each Z, which may be the same or different, is oxygen or sulphur, and
one or two of the atoms, a, b, c and d are nitrogen atoms and the remainder are carbon atoms, $R^9$ having no significance when two of a, b, c and d are nitrogen,
(with certain exclusions)
and pharmaceutically acceptable derivatives thereof.

There are also described methods for making the compounds and pharmaceutical, e.g. anti-allergic, compositions and mixtures containing them.

31 Claims, No Drawings

PYRANOQUINOLINONES AND ANALOGS THEREOF

This is a continuation, of application Ser. No. 82,994, filed Oct. 9, 1979 now abandoned.

This invention relates to new nitrogen heterocyclic derivatives, compositions containing them and methods for their preparation.

According to our invention we provide compounds of formula I,

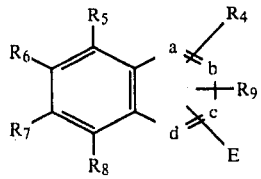

in which
an adjacent pair of $R_5$, $R_6$, $R_7$ and $R_8$ form a chain $-CZC(G_1)=C(G_2)-Z-$,
$R_4$, $R_9$ and the remainder of $R_5$, $R_6$, $R_7$ and $R_8$, which may be the same or different, each represent hydrogen, alkyl, halogen, alkenyl, $-NO_2$, $-NR_1R_2$, $-OR_3$, $-S(O)_nR_3$; or alkyl substituted by hydroxy, amino, alkoxy or carbonyl oxygen,
n is 0, 1 or 2,
$R_1$ and $R_2$, which may be the same or different, each represent hydrogen, alkyl, $-OONHR_3$, phenyl or phenyl substituted by alkyl or halogen, or $R_1$ and $R_2$ together with the nitrogen atom to which they are attached form a 5 or 6 membered heterocyclic ring,
$R_3$ represents hydrogen, alkyl, alkenyl or phenyl,
one of $G_1$ and $G_2$ is hydrogen and the other is a group E,
each E, which may be the same or different, is $-COOH$, a 5-tetrazolyl group, or a group of formula II, $$-CONR_{10}-C-N-R_{11}$$
$$\phantom{-CONR_{10}-C}\Vert\phantom{N-R_{11}}$$
$$\phantom{-CONR_{10}-C}N\phantom{xx}N$$
$$\phantom{-CONR_{10}-CN}\diagdown\diagup$$
$$\phantom{-CONR_{10}-CNN}N$$

$R_{10}$ and $R_{11}$ are the same or different and are hydrogen, alkyl, alkenyl, phenylalkyl, alkanoyl or alkoxy carbonyl, and $R_{10}$ is hydrogen when $R_{11}$ is hydrogen,
each Z, which may be the same or different, is oxygen or sulphur, and
one or two of the atoms a, b, c and d are nitrogen atoms and the remainder are carbon atoms, $R^9$ having no significance when two of a, b, c and d are nitrogen,
provided that when (i) a, b and c are carbon atoms and d is an N atom, (ii) E is in a position ortho to the N atom and is $-COOH$, a 5-tetrazolyl group or an unsubstituted (N-tetrazol-5-yl) carboxamido group, (iii) $R_9$ is hydrogen, (iv) $G_1$ is hydrogen and $G_2$ is a group E, (v) $R_5$, $R_6$, $R_7$ and $R_8$ ar selected from hydrogen, hydroxy, alkyl, halogen, alkenyl, alkoxy or $-NR_1R_2$, and (vi) each Z is oxygen, then $R_4$ is not an $-OH$ group para to the N atom, and pharmaceutically acceptable derivatives thereof.

According to our invention we also provide a process for the production of a compound of formula I, or a pharmaceutically acceptable derivative thereof, which comprises (a) producing a compound of formula I in which both E groups are $-COOH$ by selectively hydrolysing or oxidising a corresponding compound of formula III,

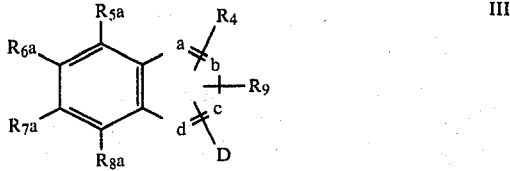

in which
$R_{5a}$, $R_{6a}$, $R_{7a}$ and $R_{8a}$ have the same significances as $R_5$, $R_6$, $R_7$ and $R_8$ above, save that an adjacent pair of $R_{5a}$, $R_{6a}$, $R_{7a}$ and $R_{8a}$ may represent a chain of formula $-CZC(J_1)=C(J_2)Z-$,
one of $J_1$ and $J_2$ is hydrogen and the other is a group $D_1$,
one or both of D and $D_1$ represents a group hydrolysable or oxidisable to a $-COOH$ group, and the other may represent a $-COOH$ group,
and a, b, c, d, $R_4$, $R_9$, Z and the proviso are as defined above, (b) producing a compound of formula I in which Z is carbonyl oxygen at the 4-position of the pyran or thiopyran ring, by cyclising a corresponding compound of formula IV,

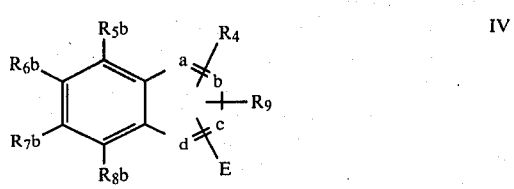

or an ester thereof, in which
$R_{5b}$, $R_{6b}$, $R_{7b}$ and $R_{8b}$ have the same significances as $R_5$, $R_6$, $R_7$ and $R_8$ above, save that an adjacent pair of $R_{5b}$, $R_{6b}$, $R_{7b}$ and $R_{8b}$, instead of forming a chain $-CZC(G_1)=C(G_2)-Z-$, represent the pairs of groups:
(i) $-COCH=CER$ or $-COCH(SOR_{13})-CH(OH)-COR''$, and $-OM$ or halogen, or
(ii) $-H$, and $-Z-C(COR'')=CH-COR''$ or $-Z-CH=C(COR'')_2$,
R represents $-R''$, halogen, $-S(O)_nR_3$ or an amino group, each $R''$, which may be the same or different, represents $-OM$, or a group which is hydrolysable thereto,
M represents hydrogen or an alkali metal,
$R_{13}$ represents alkyl or phenyl, and
a, b, c, d, $R_4$, E, $R_3$, $R_9$, n and the proviso are as defined above,
and if necessary or desired hydrolysing the group $-COR''$, to a group $-COOM$, (c) producing a compound of formula I in which at least one E group is a 5-tetrazolyl group by reacting a corresponding compound of formula I in which at least one E group is $-CN$, with an azide in a solvent which is inert under the reaction conditions, (d) producing a compound of formula I in which at least one E group is a group of formula II by reacting a corresponding compound of formula I in which at least one E group is —COOH, or an acid halide, ester or mixed anhydride thereof,
with a compound of formula V,

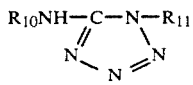      V in which $R_{10}$ and $R_{11}$ are as defined above, (e) producing a compound of formula I in which at least one of $R_4$, $R_9$ and the remainder of $R_5$, $R_6$, $R_7$ and $R_8$ is halogen by selective halogenation of a corresponding compound of formula VI,

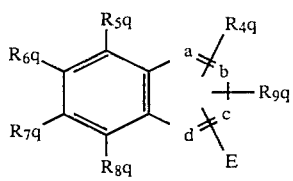      VI or an ester or N-oxide thereof, in which
a, b, c, d and E are as defined above, and
$R_{4q}$, $R_{9q}$, $R_{5q}$, $R_{6q}$, $R_{7q}$ and $R_{8q}$ have the same significances as $R_4$, $R_9$, $R_5$, $R_6$, $R_7$ and $R_8$ above, save that at least one of $R_{4q}$, $R_{9q}$, $R_{5q}$, $R_{6q}$, $R_{7q}$ represents a group Q which may be replaced by halogen, (f) producing a compound of formula I in which a, b and c are carbon and d is an N atom, $R_9$ is hydrogen, $R_4$ is hydroxy or halogen para to the N atom and E is —COOH, or an ester thereof, ortho to the N atom, or,
producing a compound of formula I in which c and d are nitrogen, E is —COOH, or an ester thereof, attached to position b and $R_4$ is hydroxy or halogen attached to position a,
by selective cyclisation and, when $R_4$ is to be halogen, concomitant halogenation of a corresponding compound of formula VII,

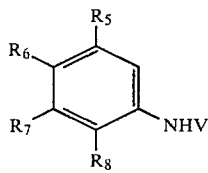      VII in which V represents a group —C(COR″)=CH(-COR″), —CH=C(COR″)$_2$ or —N=C(COR″)$_2$ respectively, and
$R_5$, $R_6$, $R_7$, $R_8$, R″ and the proviso are as defined above, (g) producing a compound of formula I in which at least one of $R_4$, $R_9$ and the remainder of $R_5$, $R_6$, $R_7$ and $R_8$ represents —O$R_{3a}$, in which $R_{3a}$ is alkyl, alkenyl or phenyl, by reacting a corresponding compound of formula I, or an ester thereof, in which $R_4$, $R_9$ and the remainder of $R_5$, $R_6$, $R_7$ and $R_8$ are as defined above, save that at least one of $R_4$, $R_9$ and the remainder of $R_5$, $R_6$, $R_7$ and $R_8$ represents —OH and the proviso does not apply, with a compound of formula VIII, $R_{3a}G$      VIII in which $R_{3a}$ is as defined above, and
G is a leaving group, (h) producing a compound of formula I in which $R_4$ is ortho or para to an N atom and represents —O$R_3$, —S$R_3$ or —N$R_1R_2$, by reacting a corresponding compound of formula I, or an ester thereof, in which $R_4$ represents a leaving group, with a compound of formula IX or X respectively, $R_3ZH$      IX $HNR_1R_2$      X in which Z, $R_1$, $R_2$ and $R_3$ are as defined above, (i) selectively removing the groups A and B from a compound of formula XI,

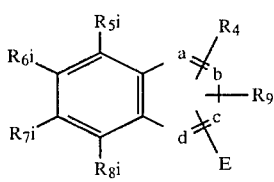      XI in which
$R_{5i}$, $R_{6i}$, $R_{7i}$ and $R_{8i}$ have the same significances as $R_5$, $R_6$, $R_7$ and $R_8$ above, save that an adjacent pair of $R_{5i}$, $R_{6i}$, $R_{7i}$ and $R_{8i}$ represent a chain of formula —CZCA(G$_1$)—CB(G$_2$)—Z—,
Z, $G_1$, $G_2$, a, b, c, d and the proviso are as defined above, and
one or both of A and B is hydrogen, halogen, hydroxy, alkoxy or acyloxy, (j) producing a compound of formula I in which at least one of $R_1$, $R_2$, $R_3$, $R_4$, $R_5$, $R_6$, $R_7$, $R_8$ and $R_9$ is alkyl by
(i) selective reduction of a corresponding compound of formula I in which the corresponding group $R_1$, $R_2$, $R_3$, $R_4$, $R_5$, $R_6$, $R_7$, $R_8$ and $R_9$ is a group reducible to an alkyl group, or
(ii) selective alkylation of a corresponding compound of formula I in which at least one of $R_1$, $R_2$, $R_3$, $R_4$, $R_5$, $R_6$, $R_7$, $R_8$ and $R_9$ is hydrogen, (k) producing a compound of formula I in which at least one of $R_4$, $R_5$, $R_6$, $R_7$, $R_8$ and $R_9$ is allyl or allyl substituted by alkyl ortho or para to another one of $R_4$, $R_5$, $R_6$, $R_7$, $R_8$ and $R_9$ which is hydroxy, by subjecting a corresponding compound of formula I in which at least one of $R_4$, $R_5$, $R_6$, $R_7$, $R_8$ and $R_9$ is hydrogen ortho or para to another one of $R_4$, $R_5$, $R_6$, $R_7$, $R_8$ and $R_9$ which is an allyl ether group or an alkyl substituted allyl ether group, to an elevated temperature, (l) producing a compound of formula I in which at least one of $R_4$, $R_5$, $R_6$, $R_7$, $R_8$ and $R_9$ is a group —NH$_2$ by selective reduction of a corresponding compound of formula I in which at least one of $R_4$, $R_5$, $R_6$, $R_7$, $R_8$ and $R_9$ represents —NO$_2$, (m) producing a compound of formula I in which Z in the 4-position of the pyrone or thiopyrone ring is carbonyl oxygen, by conversion of a compound of formula XII,

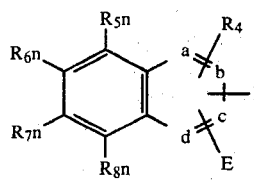

or an ester thereof, in which $R_{5n}$, $R_{6n}$, $R_{7n}$ and $R_{8n}$ have the same significances as $R_5$, $R_6$, $R_7$ and $R_8$ above, save that an adjacent pair of $R_{5n}$, $R_{6n}$, $R_{7n}$ and $R_{8n}$ represent a chain of formula $-C(R_{14}R_{15})C(G_1)=C(G_2)-Z-$, in which $R_{14}$ and $R_{15}$ together form a group $=S$ or together form a chain $-Ta(CH_2)_xTa-$, in which each Ta, which may be the same or different represents $-S-$, $-O-$ or $-NH-$, and x is 1, 2 or 3, or $R_{14}$ and $R_{15}$ together form a group $=CR_{16}R_{17}$ in which $R_{16}$ and $R_{17}$, which may be the same or different each represent hydrogen; alkyl; nitrile; carboxyester; cycloalkyl; or phenyl optionally substituted by halogen, hydroxy, alkyl, haloalkyl, hydroxyalkyl, or alkoxy-alkyl; or $R_{16}$ and $R_{17}$ together with the carbon atom to which they are attached form an alicyclic ring, and a, b, c, d, $R_4$, $R_9$, $G_1$, $G_2$, Z and the proviso are as defined above, to a corresponding compound of formula I, (n) producing a compound of formula I in which at least one of $R_4$, $R_5$, $R_6$, $R_7$, $R_8$ and $R_9$ is $-H$ by (i) selective reduction of a corresponding compound of formula I in which at least one of $R_4$, $R_5$, $R_6$, $R_7$, $R_8$ and $R_9$ is halogen or a group $-SR_3$, or (ii) selective removal of a blocking group from a corresponding compound of formula I, or an ester thereof, in which at least one of $R_4$, $R_5$, $R_6$, $R_7$, $R_8$ and $R_9$ represents a blocking group, (o) producing a compound of formula I in which $R_4$ and $R_9$, which may be the same or different, are hydrogen, alkyl or alkenyl, by selectively removing the groups A and B from a compound of formula XXVI,

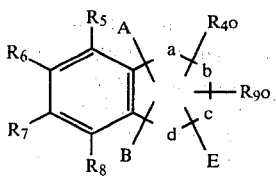

in which $R_5$, $R_6$, $R_7$, $R_8$, E, A and B are as defined above, $R_{40}$ and $R_{90}$, which may be the same or different, are hydrogen, alkyl or alkenyl, and an adjacent pair of a, b, c and d are joined by a double bond, (p) producing a compound of formula I in which $R_1$ represents hydrogen or alkyl and $R_2$ represents $-CONHR_3$ by reacting a corresponding compound of formula I in which $R_1$ represents hydrogen or alkyl and $R_2$ represents hydrogen with a compound of formula $R_3NCO$, or with phosgene and an amine of formula $R_3NH_2$, or by reacting a compound of formula I in which $R_1$ represents hydrogen and $R_2$ represents $-CONH_2$ with an amine $R_3NH_2$, $R_3$ being as defined above, (q) producing a compound of formula I in which a and d are both nitrogen, E is a COOH group, or an ester thereof, attached to position b and $R_4$ is $-OH$ attached to position c, by reacting a compound of formula XIV,

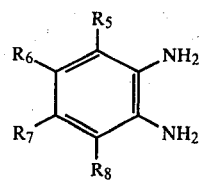

in which $R_5$, $R_6$, $R_7$ and $R_8$ are as defined above, with alloxan or mesoxalic acid, or an ester thereof, (r) producing a compound of formula I in which b and d are both nitrogen atoms, E is $-COOH$, or an ester thereof, attached to position c and $R_4$ is $-OH$ attached to position a, by (i) cyclising a compound of formula XV,

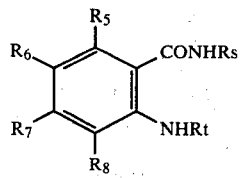

in which one of Rs and Rt is hydrogen and the other is a group $-COCOR''$, and $R_5$, $R_6$, $R_7$, $R_8$ and R'' are as defined above, or (ii) reaction of a compound of formula XIII,

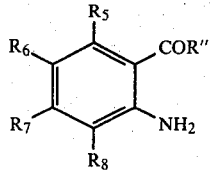

in which $R_5$, $R_6$, $R_7$, $R_8$ and R'' are as defined above, with a compound of formula XXV,

NCCOR''  XXV in which R'' is as defined above, (s) producing a compound of formula I in which at least one of $R_4$, $R_5$, $R_6$, $R_7$, $R_8$ and $R_9$ is a group $-S(O)_mR_3$ in which m is 1 or 2, and $R_3$ is as defined above, by selective oxidation of a corresponding compound of formula I in which at least one of $R_4$, $R_5$, $R_6$, $R_7$, $R_8$ and $R_9$ is a group $-S(O)_pR_3$, and p is 0 or 1 respectively, or (t) producing a pharmaceutically acceptable salt of a compound of formula I, by treating a compound of formula Ia,

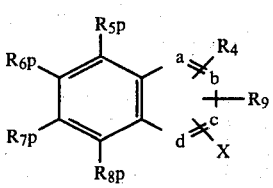

in which

R$_{5p}$, R$_{6p}$, R$_{7p}$ and R$_{8p}$ have the same significances as R$_5$, R$_6$, R$_7$ and R$_8$ above, save that an adjacent pair of R$_{5p}$, R$_{6p}$, R$_{7p}$ and R$_{8p}$ may form a chain —Z—C(X$_1$)=C(X$_2$)CZ—, one of X$_1$ and X$_2$ is hydrogen and the other is an X group, and X is a group E (or an ester thereof, or another salt thereof), a nitrile group, an acid halide group or an amide group, and a, b, c, d, R$_4$, R$_9$, Z and the proviso are as defined above, with a compound containing an available pharmaceutically acceptable cation and capable of converting the group X to a pharmaceutically acceptable salt of an E group, and if necessary or desired converting the compound of formula I to a pharmaceutically acceptable derivative thereof or vice versa.

In process (a) the groups D and/or D$_1$ may be, for example an ester, acid halide, amide or a nitrile group, which may be hydrolysed to a —COOH group. The hydrolysis may be carried out using conventional techniques, for example under mildly basic conditions, e.g. using sodium carbonate, sodium hydroxide, sodium bicarbonate, or under acidic conditions, e.g. hydrogen bromide in acetic acid. When the group D and/or D$_1$ is an ester group we prefer to carry out the hydrolysis under basic conditions, e.g. using sodium hydroxide in an alkanol, e.g. methanol. The hydrolysis may be carried out at a temperature of from about −5° to 120° C. depending on the compounds used. Alternatively the group D may be an alkyl, e.g. a lower alkyl such as methyl; a hydroxymethyl, an aralkenyl, e.g. styryl; an acyl, e.g. a lower alkanoyl such as acetyl; or a formyl group. The oxidation may be carried out using conventional techniques which do not otherwise modify the molecule to such an extent that the yield of the desired product is uneconomical, for example an alkyl or a hydroxymethyl group may be oxidised using selenium dioxide, e.g. under reflux in aqueous dioxan; or chromic acid, e.g. under reflux in aqueous acetic acid. Aralkenyl groups may be oxidised using, for example ozone or neutral or alkaline potassium permanganate in aqueous ethanol, and acyl groups may be oxidised using, for example chromic acid or an aqueous hypochlorite, e.g. sodium hypochlorite. The formyl group may be oxidised using, for example chromic acid or silver oxide.

When one of the groups is —OM the cyclisation of process (b)(i) may be carried out by heating, or under basic or neutral conditions. It is however preferred to carry out the cyclisation in the presence of an acid, e.g. gaseous or aqueous HCl, and in a solvent which is inert under the reaction conditions, e.g. ethanol or dioxan. The reaction may be carried out at from about 20° to 150° C. The group —COR″ is preferably an ester group, e.g. R″ may be a lower alkoxy group. When one of the groups is halogen the cyclisation may be carried out in a solvent which is inert under the reaction conditions, preferably a high boiling polar solvent, e.g. pyridine, dimethylformamide or hexamethylphosphoramide. The reaction is preferably carried out with the aid of a strong base, for example an alkali metal hydride, e.g. sodium hydride. The reaction is preferably carried out at a temperature of from about 80° to 200° C., in the absence of free oxygen, e.g. under an inert atmosphere such as nitrogen. R may represent an unsubstituted or a mono- or di- C 1 to 6 alkyl- or aryl-, e.g. a phenyl-, amino group or an amino group forming part of a heterocyclic, e.g. a piperidine, ring. R$_{13}$ preferably contains 1 to 6 carbon atoms. We prefer E to be —COOH or an ester thereof. In particular we prefer the group —COCH=CER to be —COCH=C(OH)—COR″.

The cyclisation of process (b)(ii) may be carried out by heating or by treating the compound of formula III with a cyclising agent, for example a dehydrating agent such as sodium bisulphate or chlorosulphonic, polyphosphoric or sulphuric acid. The reaction is preferably carried out under anhydrous conditions and may be carried out at a temperature of from −30° to 100° C. Alternatively cyclisation may be achieved by converting the free carboxy groups (i.e. when R″ is hydroxy) of the compound of formula III to acyl halide groups and subjecting the resulting acyl halide to an intramolecular Friedel-Crafts reaction. In this process the two groups R″ may be different, but are preferably the same.

Processes b(i) and b(ii) usually yield the free acid of formula I or an ester thereof.

Suitable solvents which are inert under the reaction conditions of process (c) include those in which both the reagents are soluble, e.g. N,N-dimethylformamide, dimethylsulphoxide, tetrahydrofuran, diethyl glycol and ethyl methyl glycol. The reaction is preferably carried out at a temperature of from about 20° to 130° C. for from about 1 to 20 hours. The azide used in the reaction is preferably ammonium or an alkali metal azide, e.g. sodium or lithium azide. Where an azide other than that of an alkali metal is used this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above, the reaction may be carried out using hydrazoic acid (hydrogen azide) at a temperature of from about 20° to 150° C. in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid.

In process (d) the anhydride is preferably a mixed anhydride of such a type that it will cleave preferentially to give the desired carboxamidotetrazole as the major product. Suitable acids from which the mixed anhydride may be derived are sulphonic acids e.g. benzene sulphonic acid, sterically hindered carboxylic acids, e.g. pivalic acid, and lower alkoxy formic acids, e.g. ethoxy or isobutoxy formic acid or ethyl chloroformate. When an acid halide is used it may conveniently be an acid chloride. The reaction is preferably carried out under anhydrous conditions in an inert solvent, e.g. pyridine or dimethylformamide. The reaction is preferably carried out in the presence of an acid acceptor, e.g. triethylamine. The reaction is preferably carried out at a temperature of from about 0° to 60° C. When an ester is used we prefer to use a lower alkyl ester or a nitrophenyl ester, e.g. a p-nitrophenyl ester, and to carry out the reaction in a solvent which is inert under the reaction conditions, e.g. dimethylformamide or glacial acetic acid, at a temperature of from about 20° to 150° C. When a compound of formula I in which E is —COOH is used as starting material the reaction may be carried out in the presence of a condensation agent, e.g. N,N′-carbonyldiimidazole or dicyclohexyl carbodiimide, in an aprotic solvent, e.g. dimethylformamide, at a temperature of from about 10° to 40° C. We prefer the compound of formula V to be 5-aminotetrazole.

In process (e) the group Q may be a group $-OR_3$ or $-SR_3$ (or a sulphonyl or sulphinyl derivative thereof), a nitro group or hydrogen (when an N-oxide is used), another halogen atom, e.g. a fluorine atom, or a diazonium group. We prefer the group Q to be an $-OH$ group. The selective halogenation may be carried out using a source of halogen, for example chlorine or a phosphorus oxyhalide, e.g. phosphorus oxychloride or phosphorus oxybromide or a phosphorus tri or penta halide, e.g. $PCl_3$ or $PCl_5$, or thionyl chloride. When Q is a diazo group the source of halogen may be, for example, a cuprous halide, e.g. cuprous chloride. The reaction may be carried out in a solvent which is inert under the reaction conditions, e.g. benzene, decalin or a chlorinated hydrocarbon solvent; the reaction is also preferably carried out under anhydrous conditions. The reaction is preferably carried out at a temperature of from 25° to 200° C. We prefer to use a compound of formula VI or an ester thereof. We prefer only one of $R_4$ and $R_9$ to be a group Q and for that group to be ortho or para to an N atom.

Process (f), when it involves halogenation, may be carried out under substantially the same reaction conditions as process (e), preferably using a phosphorous trichloride or a phosphorus oxychloride as a combined and simultaneous dehydrating and halogenating agent. When no halogenation is involved a dehydrating agent such as chlorosulphonic, sulphuric or polyphosphoric acid may be used or the cyclisation may be effected by heat, e.g. in a suitable high boiling solvent.

In process (g) the leaving group is preferably an anion forming group, e.g. a chlorine, bromine or iodine atom or methane sulphonate or p-toluenesulphonate group. The reaction is preferably carried out in the presence of a strong base, e.g. sodium hydride, and in a solvent which is inert under the reaction conditions, e.g. dimethylformamide. The reaction is preferably carried out under anhydrous conditions in the absence of oxygen, e.g. under a dry nitrogen atmosphere. The reaction may be carried out at from about 0° to 50° C. We prefer not to use process (g) for the production of compounds in which the group E is in the position meta to the nitrogen atom.

In process (h) the reaction may be carried out in a solvent which is inert under the reaction conditions, e.g. dimethylformamide or ethanol, at an elevated temperature, e.g. of 25° to 200° C. The leaving group may be as described with respect to process (g), e.g. halogen, phenoxy or alkylsulphonyl.

When both A and B are hydrogen process (i) is a dehydrogenation and may be carried out catayticaly, e.g. using Pd/C at an elevated temperature, or by oxidation using a mild oxidising agent, for example selenium dioxide, palladium black, chloranil, lead tetraacetate, sulphur or triphenyl methyl perchlorate. Alternatively the dehydrogenation may be carried out indirectly by halogenation followed by dehydrohalogenation, e.g. by treatment with N-bromosuccinimide or pyridinium bromide perbromide to yield a compound of formula XI in which A is halogen and B is hydrogen, which is subsequently dehydrohalogenated. When one of A and B is hydroxy the dehydration may be catalysed by an acid, e.g. sulphuric or oxalic acid; a base, e.g. potassium hydroxide; or a salt, e.g. potassium hydrogen sulphate; or N-bromosuccinimide. The reaction may be carried out in a solvent which is inert under the reaction conditions, e.g. a halogenated hydrocarbon, xylene, or glacial acetic acid. The reaction may be carried out at an elevated temperature, e.g. from 20° to 150° C.

In process (j)(i) the reduction may be hydrogenation, e.g. catalytic hydrogenation, for example using a palladium on charcoal or a Raney nickel catalyst in a suitable solvent, e.g. ethanol when, as we prefer, the group to be reduced is an alkenyl or an oxo-substituted alkyl group. The reaction may conveniently be carried out at from about 20° to 80° C., preferably at greater than atmospheric pressure. Alternatively when the group to be reduced is an oxo-substituted alkyl group, e.g. a propionyl group, the reduction may be carried out using standard selective reduction techniques which will not adversely effect other parts of the molecule. Other groups which may be reduced to an alkyl group include an alkyl group substituted by an amino, hydroxy or alkoxy group.

In process (j)(ii) the alkylation may be a direct alkylation into the benzene or N-containing ring and may be effected by a corresponding lithium alkyl compound in a solvent which is inert under the reaction conditions, e.g. diethyl ether, and at a temperature of from 0° to 75° C. Alternatively the reaction may take the form of a Friedel Crafts alkylation using an alkyl halide and a Lewis acid catalyst, e.g. $AlCl_3$ or $ZnCl_2$, and an inert solvent, e.g. nitrobenzene, at an elevated temperature, e.g. of from 50° to 150° C. When a compound of formula I in which one or both or $R_1$ and $R_2$ is alkyl is desired, the process may be carried out using an appropriate alkyl halide, e.g. an alkyl iodide such as methyl iodide; an alkyl sulphate, e.g. dimethyl sulphate; a trialkoxonium borofluoride, e.g. triethyloxonium borofluoride; or an alkoxy sulphonyl fluoride, e.g. methoxysulphonylfluoride. The reaction may be carried out in a solvent which is inert under the reaction conditions, e.g. acetone or methylene chloride. The reaction may be carried out at a temperature of from about $-20°$ C. to the boiling point of the solvent employed. When the alkyl group desired is a methyl group the reaction may be carried out using formaldehyde and formic acid under reflux. The particular reagents and conditions used to effect the alkylation will depend on the starting material and the position at which alkylation is required.

In process (k) the reaction may be carried out under conditions conventional for a Claisen rearrangement, e.g. at a temperature of about 170° to 250° C. optionally in a high boiling solvent which is inert under the reaction conditions, e.g. tetrahydronaphthalene, sulpholane, N-methylpyrrolidone or a dialkyl aniline.

The reduction of process (1) may be carried out by catalytic hydrogenation, e.g. using a palladium on charcoal (5% Pd) catalyst. The hydrogenation may if desired be carried out at a temperature of from about 10° to 50° C. and at an elevated pressure, e.g. of up to about 50 atmospheres. The hydrogenation may be carried out in a solvent which is inert under the reaction conditions, e.g. ethanol, acetic acid or a mixture thereof. The reduction may also be carried out by means of a chemical reducing agent, e.g. stannous chloride in acetic and hydrochloric acid, at a temperature of from about 20° to 100° C.

In process (m) we prefer both groups Ta to be the same. When $R_{14}$ and $R_{15}$ together form a chain $-S-(CH_2)_x-S-$, the conversion may comprise oxidative hydrolysis and may be carried out in an aqueous polar organic solvent, for example aqueous ethanol, acetone or tetrahydrofuran. The oxidative hydrolysis may be carried out in the presence of an oxidising agent, for example mercuric chloride, an N-halosuccinimide such as N-bromo- or N-chloro-succinimide, a peracid such as periodic acid; or p-toluenesulphonchloramide or a salt thereof. When mercuric chloride is used the reaction may be carried out in the presence of a base, e.g. mercuric oxide, cadmium carbonate or calcium carbonate. N-halosuccinimides may be used alone or in the presence of a silver salt, e.g. silver perchlorate, or silver nitrate. The reaction may conveniently be carried out at a temperature of from about 15° to 100° C.

When $R_{14}$ and $R_{15}$ together form a $=S$ group or one of $R_{14}$ and $R_{15}$ is hydrogen and the other is $-SR_3$ the conversion may comprise (oxidative) hydrolysis and may be carried out in the presence of a heavy metal compound, e.g. a compound of a metal of group Ib, IIb or IIIb of the Periodic Table of Mendeleef, as catalyst. Suitable compounds include mercury, thallium and silver compounds, e.g. mercury (II) acetate or chloride, thallium (III) trifluoroacetate, or silver oxide. The reaction may be carried out in the presence of water and an organic solvent system such as acetone-acetic acid, alkanols, tetrahydrofuran/methanol, or tetrahydrofuran. Alternatively, the reaction may be carried out by alkylation followed by hydrolysis. In such cases the reaction may be effected by (i) an alkyl halide or sulphonate (e.g. methyl iodide), in a moist solvent, e.g. acetone, (ii) an alkylfluorosulphonate and water in sulphur dioxide, or (iii) a trialkyl oxonium fluoroborate followed by aqueous sodium hydroxide.

When $R_{14}$ and $R_{15}$ together form an $-NH(CH_2)_xNH-$ or an $-O(CH_2)_xO-$ chain, or when one of $R_{14}$ and $R_{15}$ is hydrogen and the other is $-NR_1R_2$, $-CL$ or $-OR_3$ the reaction comprises hydrolysis or oxidative hydrolysis and may be carried out under acidic or basic conditions. The reaction is preferably carried out in a polar solvent, e.g. an alkanol or water, or in an ether.

When $R_{14}$ and $R_{15}$ together form a group $=CR_{16}R_{17}$ or when one of $R_{14}$ and $R_{15}$ is $-H$ and the other is $-OH$ the reaction comprises oxidation and may be effected by an appropriate oxidising agent, e.g. a permanganate, ozone or sodium chromate. The reaction is preferably carried out in an inert solvent, e.g. acetone, an ether, or an aromatic hydrocarbon. We prefer $R_{16}$ and $R_{17}$ together to contain up to 10 and preferably up to 8 carbon atoms.

In process (n)(i) the reduction may be either chemical or catalytic. Thus when one of $R_4$ and $R_9$ is halogen the reduction may be effected by a trialkyl tin hydride or a cyanoborohydride or catalytically using, for example, a Pt/C catalyst at greater than atmospheric pressure and in a low polarity solvent which is inert under the reaction conditions, e.g. ethanol or tetrahydrofuran. When one of $R_4$ and $R_9$ is a group $-SR_3$ the reduction may be effected catalytically, for example using Raney nickel.

In process (n)(ii) the blocking group may be, for example, a carboxylic acid group, a t-butyl group, a diazonium group or an $-OH$ group. The carboxylic acid group may be removed by heating preferably in an inert solvent, e.g. quinoline, and optionally in the presence of a copper salt. The diazonium group may be removed by reduction, e.g. using aqueous phosphoric acid or cuprous oxide in ethanol. The hydroxy group may be removed by conversion to an O-phenyltetrazolyl group and catalytic reduction thereof. The t-butyl group may be removed by heating with a Lewis acid, e.g. trifluoroacetic acid, HF, aluminium chloride or silica optionally in a suitable solvent, which may also act as an acceptor, e.g. xylene.

Process (o) may be carried out under the same conditions as, and if desired simultaneously with, process (i) above.

Process (p) may be carried out in an inert solvent, e.g. toluene, at a temperature of from about 20° to 100° C. when the reaction involves phosgene or a compound $R_3NCO$. When phosgene is used the reaction may conveniently be carried out in a sealed vessel. When the process involves a starting material of formula I in which $R_1$ represents hydrogen and $R_2$ represents $-CONH_2$ the reaction may be carried out in an inert solvent, e.g. water, at a temperature of, for example, 50°–150° C.

Process (q) may be carried out in a solvent which is inert under the reaction conditions, e.g. water or ethanol. The reaction may be carried out at a temperature of from 20° to 100° C., and may, if desired, be carried out in an inert atmosphere.

Process (r)(i) may be carried out under the same conditions as, and if desired at the same time as, process (b)(i) above. When Rs is hydrogen the reaction involves rearrangement to a compound in which Rs is $-CO-COR''$ before cyclisation. Such a combined rearrangement and cyclisation is preferably carried out by heating.

Process (r)(ii) may be carried out in an acidic medium, e.g. a mixture of hydrochloric and acetic acids, at an elevated temperature of, e.g. up to 150° C.

Process (s) may be carried out using a suitable oxidising agent, e.g. a per acid, such as m-chloroperbenzoic acid, in a solvent which is inert under the reaction conditions, e.g. dichloromethane. The reaction may be carried out at a temperature of from about 10° to 60° C.

In process (t) compounds capable of converting the group X to a pharmacetically acceptable salt of an E group include compounds, e.g. bases and ion exchange resins, containing pharmaceutically acceptable cations, e.g. sodium, potassium, calcium, ammonium and appropriate nitrogen containing organic cations. In general we prefer to form the pharmaceutically acceptable salt by treating the free acid of formula I or an ester, e.g. a lower alkyl ester, thereof, with an appropriate base, e.g. with an alkaline-earth or alkali metal hydroxide, carbonate or bicarbonate in aqueous solution or by a metathetical process with an appropriate salt. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

The starting materials for processes (a) to (t) are either known, or are themselves other compounds of formula I, or may be made from known compounds using processes known per se. The production of a number of starting materials is described in the Examples and other starting materials may be made by processes analogous to those described in the Examples or analogous to processes (a) to (t) above. Techniques for the production of certain starting materials are described below.

Compounds of formula III can be made by processes analogous to processes (b) and (e) to (s). Thus compounds of formula III may be made by a process analogous to process (b) from compounds of formula IV, or their analogues in which the —COOH group is replaced by a group D. Compounds of formula III may also, for example in the case of the acid halide, the amide and the nitrile, be made from compounds of formula I using conventional techniques, e.g. reaction of an ester of the compound of formula I which ammonia to produce the amide, followed by dehydration of the amide to form the nitrile. Certain of the compounds of formula III may also be made, e.g. where $R_4$ is halogen by a process analogous to process (e) or (f); where $R_4$ is a group —$OR_3$ by a process analogous to process (g) and where $R_4$ is —$SR_3$ or —$NR_1R_2$ by a process analogous to process (h).

Compounds of formula III in which Z in the 4-position of the pyran or thiopyran ring is sulphur may be made by reacting a corresponding compound, e.g. ester, of formula III in which that Z is oxygen with phosphorous pentasulphide.

The compounds of formula IV in which an adjacent pair of $R_5b$, $R_6b$, $R_7b$ and $R_8b$ represent the groups —$COCH_2COR''$ and —OM or halogen, may be made by reacting a compound of formula XVI,

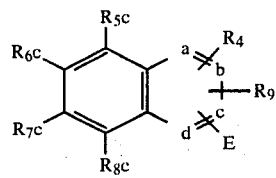
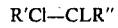

XVI or an ester thereof, in which a, b, c, d, $R_4$, E, $P_9$ and the proviso are as defined above, and $R_5c$, $R_6c$, $R_7c$ and $R_8c$ have the same significances as $R_5$, $R_6$, $R_7$ and $R_8$ above, save that an adjacent pair of $R_5c$, $R_6c$, $R_7c$ and $R_8c$, instead of representing a chain —CZC($G_1$)=C($G_2$)—Z— represent —OM or halogen and —$COCH_3$, with a compound of formula XVII, R'Cl—CLR''  XVII in which R'' is as defined above, R' is a suitable leaving group, e.g. an alkoxy, halo, amino, alkylamino, substituted amino (e.g. an arylsulphonylamino group) or substituted alkylamino group, reactive with the carbanion of the —$COCH_3$ group of the compound of formula XVI, and each L is a carbonyl oxygen atom, or one L may represent two halogen atoms and the other a carbonyl oxygen atom, and if necessary hydrolysing the resulting compound to a compound of formula IV. The preferred compounds of formula XVII are dialkyl oxalates, e.g. diethyl oxalate.

Compounds of formula IV in which an adjacent pair of $R_5b$, $R_6b$, $R_7b$ and $R_8b$ represent the groups —H and —Z—C(COR'')=CH—COR'', may be made by reacting a compound of formula XVIII,

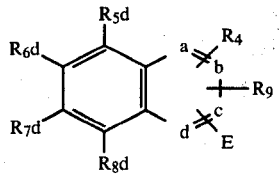
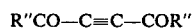

XVIII or an ester thereof, in which a, b, c, d, $R_4$, E, $R_9$ and the proviso are as defined above, and $R_5d$, $R_6d$, $R_7d$ and $R_8d$ have the same significances as $R_5$, $R_6$, $R_7$ and $R_8$ above, save that an adjacent pair of $R_5d$, $R_6d$, $R_7d$ and $R_8d$, instead of representing a chain —CZC($G_1$)=C($G_2$)—Z— represent —H and —ZM, with a compound of formula XIX,

R''CO—C≡C—COR''  XIX in which R'' is as defined above.

Compounds of formula IV in which an adjacent pair of $R_5b$, $R_6b$, $R_7b$ and $R_8$ b represent —H and —S—CH=C(COR'')$_2$ may be made by reacting a compound of formula XVIII with, for example, a dialkyl alkoxymethylenemalonate, e.g. diethyl ethoxymethylenemalonate.

Compounds of formula XVI and XVIII in which $R_4$ is other than —OH may, for example, be made by processes analogous to process (e), (g) and (h) above from corresponding compounds of formulae XVI and XVIII in which $R_4$ is —OH or, when a process analogous to process (h) is used, $R_4$ is halogen. Compounds of formulae XVI and XVIII in which a, b, and c are carbon, d is nitrogen $R_4$ is —OH para to the N atom and E is —COOH ortho or meta to the N atom are either known, or may be made by the processes of the invention, or may be made from known compounds using conventional techniques known per se. Compounds of formula XVI and XVIII in which a, b and c are carbon, d is nitrogen, E is —COOH para to the N atom and $R_4$ is —OH ortho to the N atom may be made by reacting a compound of formula XX,

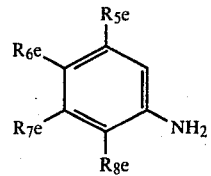
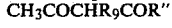

XX in which $R_5e$, $R_6e$, $R_7e$ and $R_8e$ have the same significances as $R_5$, $R_6$, $R_7$ and $R_8$ above, save that an adjacent pair of $R_5e$, $R_6e$, $R_7e$ and $R_8e$, instead of representing a chain —CZC($G_1$)=C($G_2$)—Z— represents —H and —ZM or —$COCH_3$ and —OM, with a compound of formula XXI, $CH_3COCHR_9COR''$  XXI in which $R_9$ and R'' are as defined above, to form a compound of formula XXII,

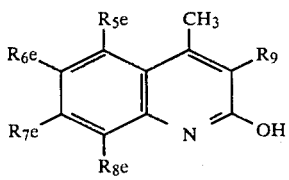

XXII in which
R$_9$, R$_{5e}$, R$_{6e}$, R$_{7e}$ and R$_{8e}$ are as defined above, (a Conrad-Limpach reaction),
followed by oxidation of the —CH$_3$ group to a —COOH group.

Compounds of formulae XVI and XVIII in which a, b and c are carbon, d is nitrogen, E is —COOH meta to the N atom and R$_4$ is —OH ortho to the N atom may be made by the following reaction in which R$_{5e}$, R$_{6e}$, and R$_{8e}$ are as defined above:

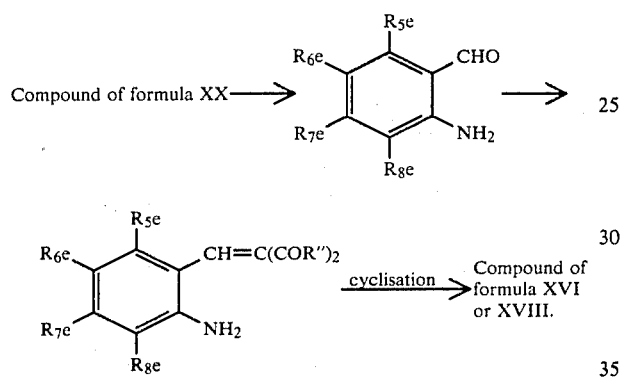

Compounds of formula XVI or XVIII in which a, b and c are carbon, d is nitrogen, R$_4$ is —OH meta to the N atom and E is —COOH ortho to the N atom may be made, for example, by the following reaction:

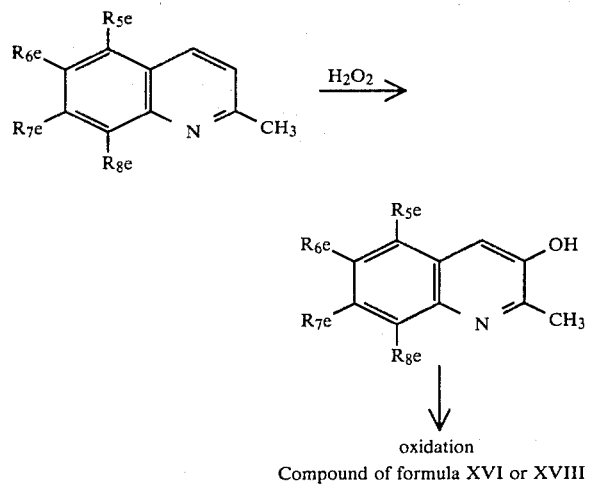

in which R$_{5e}$, R$_{6e}$, R$_{7e}$ and R$_{8e}$ are as defined above.

Other compounds of formulae XVI and XVIII may be made by processes analogous to processes (q) and (r) above.

Compounds of formula VI are either known or may be made by processes analogous to process (b) above using starting materials of formula XVI or XVIII in which, for example, R$_4$ is —Q, (e.g. —OH), methods for the production of which are described above.

The compounds of formula I in which E is —CN may be made by dehydrating the corresponding amide or oxime, in a manner known per se, using for example phosphorous oxychloride, as dehydrating agent. The amide starting material may be made by reacting a corresponding ester with ammonia, using techniques conventional in the production of amides from esters, e.g. using an alkanol as solvent at a temperature of 0° to 120° C.

Intermediates, e.g. of formulae VI, XVI and XVIII, in which E is a 5-tetrazolyl group or a group of formula II may be made from corresponding compounds in which E is —COOH by methods analogous to processes (c) and (d) above. In the case of processes analogous to process (c) the compounds in which E is —CN may be made in the same manner as described immediately above.

Compounds of formula VII may be made from a compound of formula XXIII,

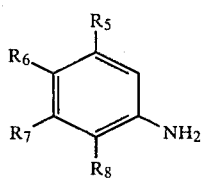

XXIII in which R$_5$, R$_6$, R$_7$, R$_8$ and the proviso are as defined above, by a process analogous to that described above for the production of a compound of formula IV from compounds of formulae XVIII and XIX.

Compounds of formulae III, VI, XVI and XVIII carrying an —OH group ortho or para to an allyl or alkyl substituted allyl group may be made by alkenyloxylation of a corresponding —OH substituted compound followed by Claisen rearrangement of the resulting alkenyloxy substituted compound (see process (k) above). The allyl or alkyl substituted allyl compounds may be reduced to give the corresponding alkyl substituted compounds.

Intermediate compounds in which R$_4$ is hydrogen may be made by reduction, e.g. catalytically or chemically, of a corresponding compound in which R$_4$ is halogen or an alkylthio group.

Compounds of formula XI may be made by methods known per se for the production of chromanones, e.g. by selective reduction of a corresponding compound of formula I.

Compounds of formula XII may be made by introduction of the —C(R$_{14}$R$_{15}$)— group at an early stage of the synthesis, using techniques known per se, and then by following the appropriate processes analogous to processes (a), (c) to (l), or (n) to (r) above.

Compounds of formula XIV may be made by nitration of a corresponding protected mono-amino compound, deprotection and reduction of the nitro group.

Compounds of formula XV may be made by a process analogous to that described above for the production of a compound of formula IV from compounds of formulae XVI and XVII.

Compounds of formulae V, IX, X, XIII, XVII, XVII, XIX, XX, XXI and XXV are either known or may be made from known compounds using conventional techniques known per se.

The processes as described above may produce the compound of formula I or a derivative thereof. It is also within the scope of this invention to treat any derivative so produced to liberate the free compound of formula I, or to convert one derivative into another.

The compounds of formula I and the intermediates therefore may be isolated from their reaction mixtures using conventional techniques.

Pharmaceutically acceptable derivatives of the compounds of formula I include pharmaceutically acceptable salts, and when E is a —COOH group, esters and amides of the 2-carboxylic acid group. Suitable salts include ammonium, alkali metal (e.g. sodium, potassium and lithium) and alkaline earth metal (e.g. calcium or magnesium) salts, and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, with simple monocyclic nitrogen heterocyclic compounds, e.g. piperidine or morpholine, with an amino acid, e.g. lysine, ornithine, arginine, or an N-alkyl, especially an N-methyl derivative of any one thereof, or with an aminosugar, e.g. glucamine, N-methylglucamine or glucosamine. Specifically included are compounds in which only one E group is in salt form. Suitable esters include simple lower alkyl esters, e.g. the ethyl ester, esters derived from alcohols containing basic groups, e.g. di-lower alkyl amino substituted alkanols such as the 2-(diethylamino)-ethyl ester, and acyloxy alkyl esters, e.g. a lower acyloxy-lower alkyl ester such as the pivaloyloxymethyl ester. The pharmaceutically acceptable acid addition salts of the basic esters, and also of those compounds in which one of $R_4$, $R_5$, $R_6$, $R_7$, $R_8$ and $R_9$ is a group —$NR_1R_2$, e.g. the hydrochloride, the hydrobromide, the oxalate, the maleate or the fumarate salts, may also be used. The esters may be made by conventional techniques, e.g. esterification or transesterification. The amides may be, for example, unsubstituted or mono- or di- C 1 to 6 alkyl or phenyl amides and may be made by conventional techniques, e.g. reaction of an ester of the corresponding acid with ammonia or an appropriate amine. Other pharmaceutically acceptable derivatives are compounds which will be suitable bioprecursors (prodrugs) of the compounds of formula I and will be readily apparent to those skilled in the art and may be made from the compounds of formula I using conventional processes known per se or by processes analogous to those described above. The compounds of formula I are for the most part, highly polar and are generally eliminated from the body rapidly. However under certain circumstances they may be metabolised within the body to form new compounds. These new metabolites are included within the ambit of the invention.

We prefer each of $R_1$, $R_2$, $R_3$, $R_4$, $R_5$, $R_6$, $R_7$, $R_8$, $R_9$, $R_{10}$ and $R_{11}$, when they contain carbon, to contain up to 8, and preferably up to 4 carbon atoms. Specifically we prefer those of $R_4$, $R_5$, $R_6$, $R_7$, $R_8$ and $R_9$ which do not form part of the chain to be selected from hydrogen, methoxy, propyl, allyl, methyl, ethyl, chlorine, bromine amino, methylamino, thioethyl, propenyloxy, allyl, phenoxy, ureido and hydroxy. We also prefer $R_3$ to be hydrogen or alkyl. The —CZC($G_1$)=C($G_2$)—Z— chain may be bonded to the benzene ring in either sense and in any of the adjacent positions $R_5$, $R_6$, $R_7$, $R_8$. However, we prefer the chain to be bonded in the positions $R_6$ and $R_7$ the —Z— part of the chain being in position $R_7$. A preferred chain is —COCH=C(COOH)—Z—, particularly where Z is oxygen. We also prefer $G_1$ to be hydrogen and $G_2$ to be a group E. In particular we prefer $R_5$ to be hydrogen and $R_8$ to be alkyl, e.g. propyl. Compounds in which a and d are nitrogen, in which c and d are nitrogen or in which b and d are nitrogen are specifically provided. However, we prefer only one of a, b, c and d to be nitrogen, and more preferably for d to be nitrogen. We prefer the E group to be in the position adjacent to a ring N-atom. We also prefer both the E groups to be the same and to be —COOH groups. $R_9$ is preferably hydrogen, alkenyl or alkyl, e.g. propyl. When E is a group of formula II we prefer $R_{10}$ and $R_{11}$ to both be hydrogen. We prefer both Z groups to be oxygen.

We prefer the group $R_4$ to be para to a single N-atom at position d. We also prefer $R_4$ to be hydrogen, halogen, —$OR_3$, —$SR_3$ or —$NR_1R_2$. We particularly prefer $R_4$ to be other than —OH. When $R_4$ is halogen it may be bromine, or preferably chlorine; when $R_4$ is alkoxy we prefer it to be methoxy or ethoxy; when $R_4$ is thioalkoxy we prefer it to be ethylthio; and when $R_4$ is —$NR_1R_2$ we prefer it to be alkylamino, e.g. ethylamino or methylamino. When $R_1$ and $R_2$ together with the nitrogen atom to which they are attached form a heterocyclic ring the ring may be, for example a morpholine, piperidine or pyrrolidine ring. When $R_1$ or $R_2$ represents phenyl substituted by halogen we prefer the halogen to be chlorine and when $R_1$ or $R_2$ represents phenyl substituted by alkyl we prefer the alkyl group to contain 1 to 6 carbon atoms. The compounds of Examples 1, 3 and 4 are preferred, the compound of Example 1 being particularly preferred.

The 5-tetrazolyl group is of formula XXIV,

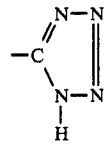

XXIV

The groups of formulae XXIV and II may exist in tautomeric forms as may certain compounds of formula I, and intermediates therefor, e.g.in which $R_4$ is —OH or —SH, which may also exist in the keto or thioketo form. Such tautomeric forms are included within the definition of the compounds of formula I.

The compounds of formula I and pharmaceutically acceptable derivatives thereof are useful because they possess pharmacological activity in animals; in particular they are useful because they inhibit the release and/or action of pharmacological mediators which result from the in vivo combination of certain types of antibody and specific antigen, e.g. the combination of reaginic antibody with specific antigen (see Example 27 of British Patent Specification No. 1,292,601). The new compounds have also been found to inhibit the degranulation of mast cells and to interfere with reflex pathways in experimental animals and man, in particular those reflexes associated with lung function. In man, both subjective and objective changes which result from the inhalation of specific antigen by sensitised subjects are inhibited by prior administration of the new compounds. Thus the new compounds are useful in the treatment of reversible airway obstruction and/or to prevent the secretion of excess mucous. The new compounds are thus useful for the treatment of allergic asthma, so-called 'intrinsic' asthma (in which no sensitivity to extrinsic antigen can be demonstrated, e.g. exercise etc, induced asthma), farmer's lung, bird fancier's disease, bronchitis, coughs (including whooping cough) and the nasal and bronchial obstructions associated with the common cold. The new compounds are also of value in the treatment of other conditions in which antigen-antibody reactions or excess mucous secretion are responsible for, or are an adjunct to, disease.

Thus the new compounds are useful in the conditions listed below in man (and corresponding conditions, where such exist, in other animals such as cattle, horses, pigs, cats or dogs):

Conditions of the outer eye including vernal catarrh, vernal conjunctivitis, vernal kerato-conjuncitivitis, ligneous conjunctivitis, blepharitis, marginal corneal ulceration of infiltration, the ocular effects of hay fever, 'allergic eyes' where the allergen is known or unknown and spring/summer conjunctivitis (this latter term is used to mean allergic disorders of the eyes occurring in the spring and summer where an external allergen plays a part in the disorder) 'irritable eye' or 'non-specific conjunctivitis', herpes simplex keratitis and conjunctivitis, herpes zoster keratitis and conjunctivitis, adenovirus infections, phlyctenular conjunctivitis, corneal homograft rejection, trachoma, anterior uveitis and drug sensitivity.

Conditions of the nose including seasonal rhinitis, e.g. hay fever; perennial rhinitis, nasal polyps and allergic manifestations of the nasopharynx.

Conditions of the ear including otitis media (glue ear).

Conditions which involve skin mast cells, basophils and/or delayed (cellular) hypersensitivity reactions, including contact dermatitis to a specific allergen, e.g. nickel, chromates, synthetic resins, applied medicaments and other chemicals (Rook A., Wilkinson DS and Ebling FJS 1972 Textbook of Dermatology 2nd Edition Blackwell, Oxford Chapters 14 and 15). Other conditions having as a component a delayed (cellular) hypersensitivity, for example autoallergic conditions, in particular thyroiditis, glomerular nephritis, nephrotic syndrome, adrenalitis, encephalomyelitis (post rabies vaccination), systemic lupus erythrematosus, rheumatoid arthritis, psoriatic arthritis, Still's disease, ankylosing spondylitis, myasthenia gravis, polymyositis, osteoarthritis, pemphigus, homograft rejection following the transplantation of tissues and organs; certain infectious diseases, in particular tuberculosis, brucellosis, staphylococcal disease, streptococcal disease and delayed allergy to toxins and vaccines. (Clinical Aspects of Immunology, (3rd Edition 1975), Eds P G H Gell, P R A Coombs, P J Lachmann, Chaps 25, 28 and 35).

Dermatoses which may be treated include contact sensitivity, e.g. to chromium, nickel or an antibiotic, eczemas, drug eruptions, psoriasis, dermatitis herpetiformis, atopic dermatitis, aphthous ulcers, Behçet's syndrome, pemphigus, urticaria, urticaria pigmentosa, the ulcers of Crohn's disease, pyoderma gangrenosum and chronic skin ulcers, notably those affecting man in tropical climates, and leg and varicose ulcers. When pemphigus, aphthous ulcers or Behçet's syndrome are to be treated the active agent may be applied to the mucous membrane.

Psychiatric conditions including those in which allergy or immune reactions (notably of the GI tract) play a contributory part, and in particular alcoholism, depression, anxiety states, mania, thought disorders, hallucinations, schizophrenia, manic depression and behavioural problems in children, e.g. hyperactivity.

Conditions of the gastrointestinal tract including aphthous ulcers, gingivitis, Crohn's disease (a condition of the small, and sometimes also of the large intestine) atrophic gastritis and gastritis variolaforme (conditions of the stomach) ulcerative colitis (a condition of the large intestine and sometimes the small intestine) proctitis, including chronic (i.e. ulcerative) and non specific proctitis (conditions of the rectum and lower large intestine), coeliac disease (a condition of the small intestine), regional ileitis (a regional inflammatory condition of the terminal ileum) peptic ulceration (a condition of the stomach and duodenum), gastro-intestinal allergy (e.g. milk, particularly cows milk, gluten and other food allergy), irritable bowel syndrome, and gastro-intestinal bleeding induced by the administration of an anti-inflammatory, for example those listed below with respect to mixtures.

Other conditions include burns, sytemic mastocytosis, CNS conditions including multiple sclerosis, migraine and cluster headache, gout, and its associated disorders, the reduction of gastric acid secretion including gastric ulcer, duodenal ulcer and anastomotic ulcer, enhancement of the output and/or bile acids content of the bile including cholelithiasis and its associated disorders, biliary stasis and disorders of bile production, and conditions such as the Mazotti reaction, following parasitic death after use of anthelmintic.

The new compounds are also useful for the prophylactic or curative treatment of a disease condition having an allergic basis in cattle, horses, pigs, cats or dogs.

Specific conditions in these animals include those in which allergy or immune reactions play a contributory part, for example certain respiratory or pulmonary conditions, in particular conditions in which antigens are involved and in which there is a shock reaction and mediators of anaphylaxis are released. Specific conditions are broken wind, heaves, chronic obstructive pulmonary disease, laminitis and sweat itch in horses; and fog fever, husk, acute bovine pulmonary emphysema, bovine farmer's lung and respiratory disease which are due, at least in part, to Respiratory Syncytial Bovine Virus (RSB) in cattle. This latter condition takes the form of an influenza like disease with dyspnoea, emphysema and foaming at the mouth.

In cats and dogs the compound may be used, particularly on oral or topical administration, to treat allergic conditions produced as a response to allergens contained in foods and food additives, in therapeutic agents, in parasitic fungi, produced by bacterial or fungal infection, or as a response to inhaled or contact antigen. Specific symptoms which may be mentioned include pruritis, characterised by excessive scratching, chewing, biting, licking or rubbing at the skin and an exaggerated scratch reflex or skin twitching; self inflicted lesions; other skin changes, characterised by generalised hyperaemia, papular reaction, oedematous plaques, oedema of head, vulva or extremities; and severe inflammatory changes leading to serious exudation and exfoliation over part of the body. Inhaled allergens can produce 'hay fever' and 'asthma' type reactions and also conjunctivitis especially in the dog. Allergic contact dermatitis is encountered most frequently in the dog.

The new compounds may be used to treat gastrointestinal disturbances and enteritis in young pigs and cattle and diarrhoeas of somewhat older animals which may occur during, or shortly after, the period of liquid feeding.

For the above mentioned uses the dosage administered will, of course, vary with the compound employed, the mode of administration and the treatment desired. However, in general, satisfactory results are obtained when the compounds are administered at a dosage of from 0.001 to 50 mg per kg of animal body weight in the test set out in Example 27 of British Patent Specification No. 1,292,601. For man the indicated total daily dosage is in the range of from 0.001 mg to 2,000 mg, preferably from 0.001 mg to 1,000 mg, more preferably from 0.01 mg to 200 mg and most preferably from 0.1 mg to 60 mg, which may be administered in divided doses from 1 to 6 times a day or in sustained release form. Thus unit dosage forms suitable for adminstration by inhalation or by swallowing comprise from 0.001 to 200 mg, preferably from 0.001 mg to 50 mg, more preferably 0.01 mg to 20 mg and most preferably from 0.01 mg to 10 mg of the compound preferably admixed with a solid or liquid pharmaceutically acceptable diluent, carrier or adjuvant.

The new compounds of the present invention may be used in combination with or sequentially with a wide variety of other pharmaceutically active substances. Where appropriate the new compounds may be mixed with one or more other active substances or the new compounds may be chemically linked with the other active substance(s), e.g. to form a salt or ester. The particular mixture, dose regimen or chemically linked substance used, and ratio of the active ingredients, will depend on a variety of factors including the condition to be treated, the mode of administration, the particular active ingredients and the patient concerned.

Examples of compounds with which the present compounds may be mixed or chemically linked include:

beta-stimulant bronchodilators for example, isoprenaline, rimiterol, ephedrine, ibuterol, isoetharine, fenoterol, carbuterol, clinbuterol, hexaprenaline, salmifamol, soterenol, trimethoquinol or preferably orciprenaline, terbutaline or salbutamol;

anti-histamine $H_1$ or $H_2$ receptor antagonists for example, oxatomide, trimeprazine, cyproheptadine, pheniramine, mepyramine, chlorpheniramine, brompheniramine, dimethindene, carbinoxamine, tripelennamine, triprolidine, ketotifen, clemastine, azatidine, maleate, dimethothiazine, diphenhydramine hydrochloride, diphenylpyraline hydrochloride, mebhydrolin, mequitazine, phenindamine tartrate, promethazine, pyrrobutamine, cimetidine or ranitidine;

anti-inflammatories or anti-rheumatoids such as aspirin, phenylbutazone, oxyphenbutazone, indomethacin, ibuprofen, ketoprofen, fenoprofen, naproxen, chloroquine, hydroxychloroquine, cycloquine gold salts, penicillamine, alclofenac, aloxiprin, azopropazone, benorylate, diclofenac, fenclofenac, feprazone, flufenamic acid, flurbiprofen, mefenamic acid, salsalate, sodium aurothiomalate, sulindac, tolmetin sodium, tolectin and diflusinal;

steroids such as hydrocortisone, and more active compounds such as betamethasone valerate, clobetasone butyrate, fluocinolone acetonide, fluocortolone hexanoate, beclomethasone dipropionate, hydrocortisone butyrate, diflucortolone valerate, triamcinolone acetonide, fluocinonide, desonide, flurandrenalone, flumethasone pivalate, methylprednisolone, clobetasol propionate, halcinonide, tixocortol, prednisolone and fluprednylidene-21-acetate;

vasoconstrictors and decongestants such as naphazoline, phenylephrine, ephedrine, oxymetazoline, adrenaline, methoxomine, tetrahydrozoline or xylometazoline;

methylphenidate, dexamphetamine, pemoline or a chelate thereof; kaolin;

anti-fungal agents, e.g. griseofulvin, nystatin, miconazole or econazole;

antiseptics;

narcotic and other analgesics, e.g. morphine, codeine, dextropropoxyphene, buprenorphine, dextromoramide, levorphanol, phenazocine, diflunisal, mefenamic acid, nefopam hydrochloride, piritramide, tiaramide, paracetamol or pentazocine, and their salts;

anti-cholinergics, e.g. atropine, ipratropium bromide, pilocarpine, deptropine or hycosine;

carbenoxolone sodium;

various injected substances, e.g. dextran and certain injected anaesthetics;

anthelmintics such as tri- and penta-valent antimony derivatives, suramin, niridazole, diethylcarbamazine, thiabendazole, levamisole or a pharmaceutically acceptable salt of any one thereof;

antibacterials and antibiotics such as tetracyclines, penicillins, chloramphenicol, neomycin, framycetin, sulphacetamide, propamidine isethionate, streptomycin, vancomycin, viormycin, rifamicin, novobiocin, gentamicin, erythromycin, cephaloridine, aminoglycosides, cephalosporins, cephamycins, colistin, fusidic acid, lincomycins, macrolides, nalidixic acid, nitrofurantoin and sulphonamides;

beta lactamase inhibitors, e.g. clavulanic acid;

antiviral agents such as idoxuridine;

compounds useful in the gastrointestinal tract, e.g. sulphasalazine or an aminosalicyclic acid;

xanthines;

mucolytics, e.g. guaiphenesin or methylcisteine or a salt thereof;

immuno- or cough-supressants, e.g. dextromethorphan, noscapine or isoaminile; and ant-acids.

The compounds of formula I, and pharmaceutically acceptable derivatives thereof, have the advantage that they are more efficacious or produce less undesirable side effects in certain pharmacological models, or are longer acting than compounds of similar structure of the compounds of formula I. Furthermore the compounds of formula I, and pharmaceutically acceptable derivatives thereof, are advantageous in that they are more efficaceous in interfering with reflex pathways and in inhibiting the secretion of mucous than are compounds of similar structure to the compounds of formula I.

The new compounds of the invention may be administered by a wide variety of routes and may act systemically or locally. Thus the compounds may be administered by oral or nasal inhalation to the lung, directly to the nose or eye, to the buccal cavity, oesophageally, rectally, topically to the skin or to other available surfaces of the body, by instillation into the bladder, by injection, e.g. intravenously, intramuscularly, intraperitoneally, or by surgical implant. The new compounds may be administered directly to the organ or part of the body showing symptoms or to a part remote from that showing symptoms. Thus skin conditions may be treated by direct application to the area effected, or by systemic, e.g. oesophageal, administration.

The new compounds of the invention may be used in a variety of dosing schedules, either on their own or in conjunction with one or more of the other active ingredients listed herein. Thus a priming dose of the new compound may be followed by a maintenance dose of the same or another compound of formula I. The priming dose may be substantially smaller or substantially larger than the maintenance dose. The new compounds when used in conjunction with another active ingredient may be used together with, before or after the other active ingredient depending on the desired combined effect of the compounds. The different active agents may be administered by the same or different routes.

The new compounds of the invention may exist in a variety of forms. Thus where the compounds are asymetric they may exist in optically active or racemic forms. The compounds may also exist in one or more polymorphic forms, and where this is the case the most stable polymorph at room temperature will generally be preferred for pharmaceutical purposes. The new compounds in substantially anhydrous form may be used, e.g. in the production of aerosols. The compounds may also exist in the form of one or more hydrates or solvates, e.g. with aerosol propellants or other liquid excipients. The new compounds, when used as solids, may also be prepared in a wide variety of sizes. Thus for inhalation and other uses the compounds may have a mass median diameter of from 0.01 to 10 microns, preferably from 2 to 6, and most preferably from 2 to 4, microns. Microaerosols in which a large proportion of the drug particles have a diameter of less than 1 micron may also be used. Larger sized crystals or agglomerates, e.g. granules or hard pellets, of the new compounds, which larger sized materials will tend to have higher bulk densities than the finely divided materials, may be used as intermediates in the formulation of the compounds, e.g. as tablets, or may be used on their own or for filling into capsules. The finely divided new compounds may also be agglomerated into 'soft' pellets or granules which are sufficiently strong to be packed, e.g. encapsulated, by machines and to be transported, but are sufficiently weak to be broken up to produce fine particles when used in an inhalation device.

The free acids, and the salts, of compounds of formula I with dibasic cations, tend to be less soluble in common solvents, e.g. water, than are the salts with mono-valent cations, e.g. sodium or potassium. The free acids and the dibasic salts are therefore more suited to formulations or uses where sustained or slow action is required. The mono-valent salts are also more suited to aqueous formulations and to formulations and uses where rapid release of the drug is required. The salts with large cations may form 'ion pairs' which, under certain circumstances, have advantageous properties, e.g. enhanced absorption.

Certain of the compounds of formula I and their derivatives may be sensitive to light and appropriate precautions should therefore be taken in their handling and formulation, e.g. solutions, and in particular dilute solutions, of these compounds should be handled in the dark or in lighting of an appropriate wavelength and should be packaged in opaque materials, e.g. amber glass bottles.

According to our invention we also provide a pharmaceutical composition comprising (preferably less than 80%, and more preferably less than 50% by weight of) a compound of formula I, or a pharmaceutically acceptable derivative thereof, in combination with a pharmaceutically acceptable adjuvant, diluent or carrier.

We particularly prefer the composition not to contain material capable of causing an adverse, e.g. an allergic, reaction in the patient. Materials which can cause adverse reactions are more fully described in Belgian Patent Specification No. 854,690.

Thus the new compounds may be formulated in a manner suitable for application to the skin of the animal, e.g. as an ointment, as a cream, which may be either an oil in water type, or a water in oil type, as a lotion or liniment, as a paste or gel. A semi-solid base that may be mentioned comprises a fatty alcohol/glycol mixture.

When the new compounds are to be used in aqueous solution we prefer the solution to be clear and to this end it may be necessary to make the solution with very pure water, e.g. containing very low amounts of dibasic, e.g. magnesium or calcium, ions, or to incorporate a chelating or sequestering agent in the solution. Aqueous solutions typically contain up to about 10% w/w of the new compound and may be used as drops or sprays.

When the new compounds are to be used to treat gingivitis or aphthous ulcers they may be formulated as a dentifrice composition, e.g. a toothpaste or a toothpowder, which may contain, for example an abrasive, a detergent and/or a humectant.

When the new compounds are to be used to treat the eye they may be used, for example, in the form of an aqueous solution, or an opthalmic ointment (e.g. in an oily base) or in a controlled release formulation, e.g. a device adapted to be inserted under the eyelid and to release the new compound at a controlled rate.

For oral or rectal administration the new compounds may be worked up with inorganic or organic pharmaceutically acceptable adjuvants or excipients. Examples of such adjuvants are:

For tablets, lozenges and dragees: Binders, for example, cellulosic materials, e.g. microcrystalline cellulose and methyl cellulose; disintegrating agents, for example starches, e.g. maize starch; stabilisers, e.g. against hydrolysis of the active ingredients; flavouring agents, for example sugars such as lactose; fillers; stearates and inorganic lubricants, e.g. talc.

For syrups, suspensions, emulsions or dispersions: A liquid vehicle in which the active ingredients may be dissolved or suspended, e.g. water; and suspending agents, e.g. cellulose derivatives, gums etc.

For hard or soft capsules: Diluents, e.g. lactose; glidants, e.g. stearates; inorganic materials, e.g. silica or talc; stabilisers and dispersing agents.

For suppositories: Natural or hardened oils, waxes etc. A large number of proprietary emulsifying bases are available and are suitable for use in suppositories. These include 'Witepsol' bases, consisting of hydrogenated triglycerides of lauric acid with added monoglycerides; and 'Massupol' bases, which consist of glyceryl esters of lauric acid with a very small amount of glyceryl monostearate.

For enemas: Water, sodium chloride, buffers etc, and optionally foam forming agents.

The composition may also contain further adjuvants, for example a composition for use in tablets may contain flow aids and glidants to assist in tabletting, e.g. magnesium stearate or colloidal silica; or wetting agents to assist in granulation, e.g. dioctyl sodium sulphosuccinate. The composition may also if desired contain a pharmaceutically acceptable dye or colourant, and may, if desired, be coated using conventional film or sugar coating techniques.

If desired the composition may be formulated in sustained release form, e.g. by coating the drug particles with a layer of a substance which could be expected to be slowly dissolved or digested or to act as semi-permeable membranes through which drug can diffuse when the preparations are ingested. Specifically there may be mentioned enteric coated formulations.

For administration by inhalation the new compounds may be formulated with a compressed gas, e.g. nitrogen, or a liquified propellant as a pressurised aerosol composition, the composition preferably containing from 1 to 20% w/w of the new compound. The composition also preferably contains less than about 5% w/w of water and more preferably is substantially anhydrous.

The liquified propellant is preferably a gas at room temperature (20° C.) and atmospheric pressure (760 mm of mercury), and should also be non-toxic. Among the suitable liquified propellants which may be employed are alkanes containing up to five carbon atoms, e.g. butane or pentane, or a C 1 to 6 alkyl chloride, e.g. methyl, ethyl or propyl chlorides. The most suitable liquified propellants are the fluorinated and fluorochlorinated C 1 to 3 (preferably C 1 or 2) alkanes such as are sold under the Registered Trade Mark 'Freon'. The preferred halogenated alkanes may be represented generally by the formula $C_mH_nCl_yF_z$, wherein m is an integer less than 3, n is an integer or zero, y is an integer or zero, and z is an integer, such that $n+y+z=2m+2$. Examples of these propellants are dichlorodifluoromethane (Propellant 12), 1,2-dichlorotetrafluoroethane (Propellant 114) $CClF_2.CClF_2$, trichloromonofluoromethane (Propellant 11), dichloromonofluoromethane (Propellant 21), monochlorodifluoromethane (Propellant 22), trichlorotrifluoroethane (Propellant 113), and monochlorotrifluoromethane (Propellant 13). Mixtures of the above propellants may be used to give improved vapour pressure characteristics, e.g. Propellant 11 with Propellant 12, or Propellant 12 with Propellant 114. We prefer compositions which do not contain Propellant 11. It is desirable that the vapour pressure of the propellant employed be between 35 and 70, and preferably between 3,500 and 4,550 grams per sq. cm. at 24° C.

The composition may also contain a surface active agent, e.g. a liquid or solid non-ionic surface active agent or a solid anionic surface active agent.

The preferred solid anionic surface active agent is sodium dioctyl-sulphosuccinate.

The amount of the surface active agent to be used is related to the solids content of the suspension and to the particle size of the solids.

When a liquid, non-ionic surface active agent is employed it should have an hydrophile-lipophile balance (HLB) ratio of less than 10 and preferably of from 1 to 5.

We prefer the surface active agent to comprise from 0.05 to 1.5% by weight of the total composition.

Suitable non-ionic surface active agents are phospholipids, e.g. endogenous phospholipids, the esters or partial esters of fatty acids containing from 6 to 22 carbon atoms, such as caproic, octoic, lauric, palmitic, stearic, linoleic, linolenic, oleostearic and oleic acids with a aliphatic polyhydric alcohol or its cyclic anhydride such as ethylene glycol, glycerol, erythritol, arabitol, mannitol, sorbitol, the hexitol anhydrides derived from sorbitol (the sorbitan esters sold under the Registered Trade Mark 'Spans') and the polyoxyethylene and polyoxypropylene derivatives of these esters. Mixed esters, such as mixed or natural glycerides may be employed. The preferred liquid non-ionic surface active agents are the oleates of sorbitan, e.g. those sold under the Registered Trade Marks 'Arlacel C' (Sorbitan sesquioleate), 'Span 80' (Sorbitan monooleate) and 'Span 85' (Sorbitan trioleate). Other suitable non-ionic surface active agents are sorbitan monolaurate, polyoxyethylene sorbitol tetraoleate, polyoxyethylene sorbitol pentaoleate, polyoxypropylene mannitol dioleate and lecithin.

For inhalation as a powder formulation the new compounds in finely divided form may be used in admixture with a larger sized carrier comprising particles, e.g. of up to 400 microns diameter. We prefer at least 90% by weight of the particles of the new compound to have an effective particle size below 10 microns (and preferably of from 0.01 to 10 microns), and at least 90% by weight of the particles of the carrier to have an effective particle size below 400 microns, and at least 50% by weight of the particles of the carrier to have an effective particle size above 30 microns. Effective particle size for particles below 30 microns may be measured by a Coulter counter. Effective particle size for particles above 30 microns may be measured by an Alpine air jet sieve.

Desirably, at least 95% by weight of the particles of the new compound have an effective particle size in the range 0.01 to 10 microns. Preferably at least 90%, and more desirably at least 95%, by weight thereof have an effective particle size in the range 1 to 10 microns. Suitably, at least 50% by weight of the particles of the new compound have an effective particle size in the range 2 to 6 microns.

The particle size spectrum of the carrier will depend on the particular inhalation device from which the formulation is to be dispersed. It is however desirable to avoid carrier particles of less than 10 microns in size, thus minimising the number of non-drug particles which penetrate deep into the lung. A large proportion of very large particles may also cause a gritty feel in the mouth of the user and is therefore less preferred. Use of a carrier of large particle size may also cause problems in filling when using filling machines which involve a dosator which picks up powder by dipping into a powder bed from above. However, use of a carrier of large particle size may ease filling when using machines in which a die is filled from above, but may incline the composition to segregate during transport or storage. Thus, desirable, at least 95% by weight of the particles of carrier have an effective particle size below 400 microns. Preferably at least 50%, and more desirably at least 70%, by weight of the carrier particles have an effective particle size in the range 30 to 150, especially 30 to 80, microns.

The composition preferably contains from 2 to 50% by weight, more especially from 5 to 25% by weight, and particularly from 10 to 15% by weight of the new compound, and from 50 to 98% by weight, more especially from 75 to 95% by weight and particularly from 85 to 90% by weight of the carrier.

The finely divided new compound may be prepared in the desired particle size range for example using a ball mill, a fluid energy mill, by precipitation or by spray drying. The carrier may be prepared by spray drying or grinding and subsequently separating out the desired fraction, for example by air classification and/or sieving.

The powder compositions may be prepared by mixing the ingredients together in one or, preferably, more (e.g. two) steps in a mixer, such as planetary or other stirred mixer.

The carrier may be any non-toxic material which is chemically inert to the new compound and is acceptable for inhalation or for administration to the nose. Examples of carriers which may be used include inorganic salts, e.g. sodium chloride or calcium carbonate; organic salts, e.g. sodium tartrate or calcium lactate; organic compounds, e.g. urea or propylidone; monosaccharides, e.g. lactose, mannitol, arabinose or dextrose monohydrate; disaccharides, e.g. maltose or sucrose; polysaccharides, e.g. starches, dextrins or dextrans. A particularly preferred carrier is lactose, e.g. crystalline lactose.

The powder compositions will generally be put up in sealed gelatine, plastic or other capsules. The container is preferably loosely filled to less than about 80% by volume, preferably less than about 50% by volume, with the powder composition.

Alternatively, for inhalation the new compound may be used in pellet or granule form, wherein the pellet or granule is soft, is from 10 to 1,000, preferably 30 to 500, microns in diameter and comprises an agglomeration of individual medicament particles, at least 90% by weight of which have a diameter of less than 10 microns.

The soft pellet or granule preferably has an internal coherence such that the pellet or granule remains intact when filled into a container, e.g. a capsule, using automatic or semi-automatic filling machines, under conditions of transport and storage, and when fluidised within a container in the device from which it is intended to dispense the pellets or granules and yet may be broken up into particles of a therapeutically effective size outside the container as it discharges from the container.

We have found that satisfactory soft pellets or granules for use in insufflators of the type described in British Pat. No. 1,182,779 (commercially available under the Registered Trade Mark 'Spinhaler') and powered by human inhalation have a mean size in the range of from 50 to 250 microns, preferably a mean size in the range 120 to 160 microns and most preferably a mean size of about 140 microns.

Certain of the new compounds, mixtures or formulations of the invention may be subject to contamination or degradation in use. Thus the compounds may be admixed with one or more preservatives or sterilising agents, for example for use in multidose liquid formulations. Alternatively, the compounds may be packed in such a way as to avoid contamination or degradation, e.g. they may be packed in sealed containers designed to provide a single dose, e.g. a capsule, sachet, vial, ampoule etc, or they may be packed in an opaque or coloured container to prevent degradation by light.

The invention is illustrated, but in no way limited by the following Examples in which temperatures are in °C.

EXAMPLE 1

Disodium 6-chloro-4-oxo-10-propyl-4H-pyrano[3,2-g]quinoline-2,8-dicarboxylate (a) Ethyl 6-chloro-8-methoxycarbonyl-4-oxo-10-propyl-4H-pyrano[3,2-g]quinoline-2-carboxylate To a stirred solution of ethyl 4,6-dioxo-8-methoxycarbonyl-10-propyl-4H,6H-pyrano[3,2-g]quinoline-2-carboxylate (1 g) in dry benzene (20 mls) was added dropwise with stirring phosphoryl chloride (1.32 mls). The whole was then stirred at ambient temperature for twenty-four hours. The reaction mixture was poured into water, extracted into ethyl acetate, washed with water, dried using magnesium sulphate, filtered and volatiles removed in vacuo, affording a light brown solid which was purified by column chromatography; yielding the sub-title compound (0.62 g) as a light brown crystalline solid. M.P. 176°–178° C.

Analysis: Found: C, 59.4; H, 4.8; N, 3.4; Cl, 8.5%. $C_{20}H_{18}ClNO_6$ Requires: C, 59.5; H, 4.5; N, 3.5; Cl, 8.8%.

NMR Spectroscopy also confirms preparation of the sub-title compound.

(b) 6-Chloro-4-oxo-10-propyl-4H-pyrano[3,2-g]quinoline-2,8-dicarboxylic acid

Ethyl 6-chloro-8-methoxycarbonyl-4-oxo-10-propyl-4H-pyrano[3,2-g]quinoline-2-carboxylate (1.313 g) was suspended in refluxing methanol (300 mls) and 0.1 M sodium hydroxide solution (65 mls) was added dropwise, with stirring. The whole was then refluxed for ten minutes, cooled, poured into water and acidified. The precipitated product was extracted into ethyl acetate, washed with water, dried with magnesium sulphate, filtered and volatiles removed in vacuo, affording 1.05 g of the crude sub-title compound as a yellow solid. This yellow solid was dissolved in sodium bicarbonate solution, filtered and the filtrate acidified. The precipitated product was collected by filtration, washed with water and dried to give 0.77 g of the sub-title compound. MP 340° C.

Analysis: Found: C 56.0; H, 3.7; N, 3.87%. $C_{17}H_{12}ClNO_6$ requires: C 56.4; H, 3.3; N, 3.87%.

N.M.R. Spectroscopy also confirms preparation of the sub-title compound.

(c) Disodium 6-chloro-4-oxo-10-propyl-4H-pyrano[3,2-g]quinoline-2,8-dicarboxylate 6-Chloro-4-oxo-10-propyl-4H-pyrano[3,2-g]quinoline-2,8-dicarboxylic acid (0.629 g) suspended in water was treated with sodium bicarbonate (0.292 g) and stirred until complete dissolution occurred. The solution was filtered then treated with acetone. The precipitated product was collected by filtration and dried to give (0.6 g) of the title compound.

Analysis: Found: C, 46.6; H, 2.9; N, 3.0; Cl, 8.2%. $C_{17}H_{10}ClNa_2NO_6$ 7.4% $H_2O$ requires: C, 46.6; H, 3.1; N, 3.1; Cl, 7.9%.

N.M.R. Spectroscopy also confirms preparation of the title compound.

EXAMPLE 2

Disodium 6-methoxy-4-oxo-10-propyl-4H-pyrano[3,2-g]quinoline-2,8-dicarboxylate (a) Ethyl 6-methoxy-8-methoxycarbonyl-4-oxo-10-propyl-4H-pyrano[3,2-g]quinoline-2-carboxylate Sodium hydride (50% dispersion in oil) (0.053 g) was washed with dry ether, then suspended in dry dimethylformamide (10 mls) in a dry nitrogen atmosphere. Ethyl 8-methoxycarbonyl-4,6-dioxo-10-propyl-4H,6H-pyrano[3,2-g]quinoline-2-carboxylate (0.39 g) was dissolved in dry dimethylformamide (20 mls), then added dropwise with stirring to the above sodium hydride suspension. The whole was stirred at ambient temperature for two hours, iodomethane (0.23 mls) was added dropwise and stirring was continued at room temperature for a further two hours. The whole was then poured into water, extracted into ethyl acetate, dried with magnesium sulphate, filtered and volatiles removed in vacuo, affording a yellow solid, which was recrystallised from a cyclohexane/dichloroethane mixture, resulting in 0.2 g of the sub-title compound. M.P. 180°–182° C.

(b) 6-Methoxy-4-oxo-10-propyl-4H-pyrano[3,2-g]quinoline-2,8-dicarboxylic acid

The product of step (a) (2.355 g) was suspended in methanol (400 mls) under reflux with stirring and N/10 sodium hydroxide solution (122 mls) was added dropwise. The solution was refluxed for a further 5 mins after addition, cooled, and then poured into water (500 mls) and acidified. The precipitated product was collected by filtration, washed with water and dried to give 1.7 g of the bis acid.

The bis acid (1.7 g) was suspended in water (100 mls) and treated with sodium bicarbonate (0.8 g). The solution was filtered and the filtrate freeze dried to give 1.2 g of bis sodium salt. This was purified by reverse phase High Pressure Liquid Chromatography using methanol/aqueous ammonium acetate as eluant. The product obtained as a solution of the ammonium salt was treated with hydrochloric acid and the precipitated bis acid collected by filtration, washed with water and dried to give 0.488 g of the desired product mp 273° (dec.)

(c) Disodium 6-methoxy-4-oxo-10-propyl-4H-pyrano[3,2-g]quinoline-2,8-dicarboxylate The product of step (b) (0.408 g) was dissolved in water (80 mls) containing sodium bicarbonate (0.192 g). The solution was filtered, and the filtrate freeze dried to give 0.425 g of the title product.

Analysis: Found: C; 46.1% H; 4.5% N; 2.5%. $C_{18}H_{13}Na_2NO_7$ 14.6% $H_2O$ Requires: C; 46.1% H; 4.4% N; 3.0%.

EXAMPLE 3

6-Methylamino-4-oxo-10-propyl-4H-pyrano[3,2-g]quinoline-2,8-dicarboxylic acid (a) Dimethyl 1-(4-acetyl-3-hydroxy-2-propylphenyl)aminofumarate 4-Amino-2-hydroxy-3-propylacetophenone (19 g) and dimethyl acetylenedicarboxylate (14.5 mls; 16.8 g) in ethanol (200 mls) were refluxed for 7 hours. The solvent was removed by evaporation to give 36.4 g of the product as an oil. The structure was confirmed by NMR and MS.

(b) Methyl 6-acetyl-7-hydroxy-8-propyl-4-oxo-4H-quinoline-2-carboxylate

The product of step (a) (30 g) was added to diphenyl ether (300 mls) at reflux. The reaction mixture was refluxed for a further 5 mins after addition, cooled, and poured into a large volume of 60°–80° petroleum ether. The precipitated product was collected by filtration, washed with petroleum ether and dried to give 20 g of brown solid. A recrystallisation from a large volume of cyclohexane gave material having mp 169°–170°.

(c) Methyl 6-acetyl-4-chloro-7-hydroxy-8-propylquinoline-2-carboxylate

The product of step (b) (3 g, 0.0099 mole) was dissolved in dry benzene (50 mls), treated with phosphoryl chloride (2.5 mls) and refluxed for 1 hour. The reaction mixture was cooled, poured into water and extracted with ether, which was then washed with water and dried over magnesium sulphate. The solvent was evaporated to leave 2.8 g of yellow-brown solid. Recrystallisation from cyclohexane gave yellow needles mp 163°–164°.

(d) 6-Acetyl-7-hydroxy-4-methylamino-8-propylquinoline-2-carboxylic acid

The product of step (c) (8.9 g) was treated with 33% w/w methylamine in ethanol (100 mls) and heated in an autoclave at 100° C. for 17 hours. The reaction mixture was cooled and poured into a mixture of water and ethyl acetate. The organic layer was separated, washed with water and dried over magnesium sulphate. The solvent was evaporated to leave 9.0 g of N-methyl-7-hydroxy-1-methylamino-6-[(1-methyl-imino)ethyl]-8-propyl-quinoline-2-carboxamide.

The amide (7.0 g) was treated with 70% sulphuric acid (350 mls) and heated under reflux for ¾ hour. The reaction mixture was cooled and aqueous ammonia added with ice cooling until pH7. The gelatinous product was collected by filtration, washed well with water and dried to give 6.4 g of the sub-title compound.

(e) Ethyl 6-acetyl-7-hydroxy-4-methylamino-8-propylquinoline-2-carboxylate

The crude product of step (d) (6.4 g) in ethanol (500 mls) which had been previously saturated with hydrogen chloride gas was heated under reflux for 1 hour. The reaction mixture was cooled, made basic with 880 ammonia and extracted with ethyl acetate, which was then washed with water and dried over magnesium sulphate. The solvent was removed by evaporation to leave 8.0 g of residual yellow solid. This solid was recrystallised from ethanol to give 3.8 g of yellow needles mp 219°–220°.

(f) Diethyl 6-methylamino-4-oxo-10-propyl-4H-pyrano[3,2-g]quinoline-2,8-dicarboxylate The product of step (e) (3.6 g) and diethyl oxalate (14 g) dissolved in dry dimethylformamide (150 mls) was added to ether washed 50% sodium hydride in oil (2.3 g) suspended in dry dimethylformamide (120 mls) under nitrogen with stirring. The reaction mixture was stirred for 24 hours and then poured into water, acidified with glacial acetic acid and extracted with ethyl acetate which was then washed with water and dried. The solvent was evaporated to leave an oil which was dissolved in ethanol (300 mls), which had previously been saturated with hydrogen chloride gas, and then refluxed for 15 mins. The reaction mixture was cooled, made basic with 880 ammonia and the precipitated solid collected by filtration, washed with water and dried to give 4.1 g of product. A recrystallisation from ethanol gave 2.9 g of crystalline product mp 235°–237°.

(g) Disodium 6-methylamino-4-oxo-10-propyl-4H-pyrano[3,2-g]quinoline-2,8-dicarboxylate The product of step (f) (1.932 g) was stirred in methanol (200 mls) under reflux with the dropwise addition of N sodium hydroxide solution (9.38 mls). The reaction mixture was stirred under reflux for a further 2 hours, cooled, filtered, and the filtrate evaporated to dryness. The residue was dissolved in water (100 mls) filtered, and the filtrate treated with a large volume of acetone until precipitation was complete. The bis sodium salt was collected by filtration and dried to give 1.55 g of product.

Analysis: Found: C; 49.7% H; 4.5% N; 6.4%. $C_{18}H_{14}Na_2N_2O_6$ 8.0% $H_2O$ Requires: C; 49.7% H; 4.1% N; 6.4%.

EXAMPLE 4

6-Ethylthio-4-oxo-10-propyl-4H-pyrano[3,2-g]quinoline-2,8-dicarboxylic acid

(a) Methyl 6-acetyl-4-ethylthio-7-hydroxy-8-propylquinoline-2-carboxylate

Methyl 6-acetyl-4-chloro-7-hydroxy-8-propylquinoline-2-carboxylate (1.0 g) in dry dimethylformamide (50 mls) was added dropwise to a stirred solution of sodium thioethoxide [made by the addition of ethanethiol (0.773 g) to 50% sodium hydride in oil (0.6 g) in dry dimethylformamide (30 mls) under nitrogen]. The purple solution was stirred for 2 hours, poured into ethyl acetate and acidified with dilute hydrochloric acid. The organic layer was separated, washed with water, sodium bicarbonate solution and then dried. Evaporation of the solvent gave 0.8 g of the desired product which was recrystallised from cyclohexane to give 0.52 g of yellow needles mp 193°–195°.

(b) Ethyl 6-ethylthio-8-methoxycarbonyl-4-oxo-10-propyl-4H-pyrano[3,2-g]quinoline-2-carboxylate The product of step (a) (2.7 g) was converted to the sub-title compound, a pale yellow solid (2.35 g) by the method of Example 3(f). Structure was confirmed by NMR and MS.

(c) Disodium 6-ethylthio-4-oxo-10-propyl-4H-pyrano[3,2-g]quinoline-2,8-dicarboxylate The product of step (b) (1.958 g) was converted to the sub-title product (1.3 g) by the process of Example 3(g).

Analysis: Found: C; 51.1% H; 4.1% N; 2.9% S; 6.9%. $C_{19}H_{15}Na_2NO_6S \cdot H_2O$ Requires: C; 50.8% H; 3.8% N; 3.1% S; 7.1%

EXAMPLE 5

Diethyl 6-chloro-4-oxo-10-propyl-4H-pyrano[3,2-g]quinoline-2,8-dicarboxylate Methyl 6-acetyl-4-chloro-7-hydroxy-8-propyl-quinoline-2-carboxylate (1.0 g) and diethyl oxalate (3.7 mls) in dry dimethylformamide (25 mls) was added to ether washed 50% sodium hydride (0.65 g) suspended in dry dimethyl formamide (25 mls) under nitrogen with stirring. The reaction mixture was stirred for 5 hours at room temperature, poured into ethyl acetate, aqueous acetic acid was added and the organic layer separated, washed well with water and dried. The solvent was evaporated, the residue dissolved in dry dioxan (100 mls) and dry hydrogen chloride gas passed through the solution for 20 minutes. The reaction mixture was poured into ethyl acetate, washed well with water, saturated sodium bicarbonate solution then water again and dried. The solvent was evaporated and the residue triturated with 40–60 petroleum ether to give 0.9 g of the title product. The structure was confirmed by NMR and MS evidence. The product was converted to the free acid and the disodium salt using the techniques of Example 1(b) and (c).

EXAMPLE 6

6-Bromo-4-oxo-10-propyl-4H-pyrano[3,2-g]quinoline-2,8-dicarboxylic acid

(a) Dimethyl 4,6-dioxo-10-propyl-4H,6H-pyrano[3,2-g]quinoline-2,8-dicarboxylate A slurry of 4,6-dioxo-10-propyl-4H,6H-pyrano[3,2-g]quinoline-2,8-dicarboxylic acid, (9.0 g: 0.026 role), was stirred and heated at reflux in methanol (300 ml), for 45 minutes, during which time dry HCl gas was introduced into the mixture. After standing at room temperature overnight the preceding treatment was repeated for a further 2 hours. After cooling insoluble material was filtered off, washed with methanol and ether and dried to leave the sub-title compound as a yellow solid, (6.4 g), (66%). Mass and NMR spectra confirmed the structure.

(b) Dimethyl 6-bromo-4-oxo-10-propyl-4H-pyrano[3,2-g]quinoline-2,8-dicarboxylate A solution of the dimethyl ester from step (a), (5.5 g; 0.0148 mole), and phosphoryl bromide, (8.5 g; 0.0296 mole), in 1,2-dichloroethane, (300 ml), was stirred and heated at reflux for 3 hours. After cooling the solution was poured into methanol and evaporated to dryness. The residue was dissolved in ethyl acetate and washed with water, dil. $NaHCO_3$ solution, water again, then dried over sodium sulphate, filtered and evaporated to leave the required sub-title compound as a pink solid. This solid was purified by chromatography on silica, giving a buff coloured product, (4.5 g) mp 179°–80°, (70%).

(c) 6-Bromo-4-oxo-10-propyl-4H-pyrano[3,2-g]quinoline-2,8-dicarboxylic acid A solution of the dimethyl ester from step (b), (3.8 g, 8.75 mmole), was converted to the sub-title product, a yellow solid, (2.4 g) by the process of Example 2(d). Mass and NMR spectra were consistent with the desired structure.

| Analysis: | C | H | N |
|---|---|---|---|
| found: | 49.0% | 3.4% | 3.05% |
| $C_{17}H_{12}BrNO_6 \cdot \frac{1}{2}H_2O$ requires: | 49.1% | 3.15% | 3.37% |

(d) Disodium
6-Bromo-4-oxo-10-propyl-4H-pyrano[3,2-g]quinoline-2,8-dicarboxylate The product of step (c), (2.166 g, 5.22 mmole), was added slowly to a solution of sodium bicarbonate, (0.876 g, 10.44 mmole), in water (35 ml). The resulting solution was filtered and the filtrate was freeze-dried to give the required salt as a brown solid, (2.23 g) 93%. The NMR spectrum was consistent with the required structure.

| Analysis: | C | H | N |
|---|---|---|---|
| found: | 44.1% | 2.9% | 2.7% |
| $C_{17}H_{10}BrNNa_2O_7$ 3.6% $H_2O$ requires: | 43.7% | 2.56% | 3.0% |

EXAMPLE 7

Disodium
6-methyl-4-oxo-10-propyl-4H-pyrano[3,2-g]quinoline-2,8-dicarboxylate (a)
+2-(4-Acetyl-3-hydroxy-2-propyl)phenylamino-4-oxopentanoic acid 4-Amino-2-hydroxy-3-propyl-phenylethanone (37.2 g) was melted on a steam bath and to this was added E-4-oxo-pent-2-enoic acid (20.0 g). The mixture was then heated on a steam bath for fifteen minutes affording crude sub-title compound (53 g), a 1 gm sample of which was recrystallised from ethylacetate and dried at reduced pressure and 70° C. for five hours affording (0.2 g) of the sub-title compound M.P. 146°–148° C.

(b)
6-Acetyl-7-hydroxy-4-methyl-8-propylquinoline-2-carboxylic acid

To the product of step (a) (50.0 g), finely ground, was added polyphosphoric acid (500 mls) with vigorous stirring. The mixture was heated on a steam bath for fifteen minutes, then poured into an iced water/ethyl acetate mixture and stirred for one hour. The resulting mixture was extracted with ethyl acetate and then washed with saturated sodium bicarbonate solution. The bicarbonate solution was acidified, and extracted into ethyl acetate, dried using magnesium sulphate, filtered and the volatile material removed in vacuo affording (16.5 g) of crude sub-title compound. A 1 gm sample was recrystallised from ethanol affording (0.7 g) of the pure sub-title compound as orange needles, M.P. 125°–127° C.

(c) Ethyl
6-acetyl-7-hydroxy-4-methyl-8-propyl-quinoline-2-carboxylate

The product of step (b) (6.5 g) was dissolved in dry ethanol (500 mls). Dry hydrogen chloride gas was then bubbled into this solution until a saturated solution resulted. This solution was heated on a steam bath for 1.5 hours. The mixture was poured into water and extracted into ether. The ethereal layer was washed with water, saturated sodium bicarbonate solution, dried using magnesium sulphate and filtered. On partial removal of the solvent a yellow solid crystallised out of solution. This was filtered off affording (1.1 g) of the sub-title compound. M.P. 150°–151° C.

(d) Diethyl
6-methyl-4-oxo-10-propyl-4H-pyrano[3,2-g]quinoline-2,8-dicarboxylate Sodium metal (0.8 g) was added to dry ethanol (100 mls) and then warmed on a steam bath until reaction was complete. A suspension of the product of step (c) (4.9 g) and diethyl oxalate (8.5 mls) in dry ethanol (250 mls) was quickly added to the above preformed sodium ethoxide solution. The heating was continued for fifteen minutes and the mixture was then poured into water, acidified with dilute hydrochloric acid and extracted into chloroform. This solution was dried using magnesium sulphate, filtered and the volatile material removed in vacuo affording an oil.

A saturated solution of ethanolic hydrogen chloride (250 mls) was added to the oil and the mixture refluxed for thirty minutes, then poured into water, extracted into ethyl acetate, dried using magnesium sulphate, filtered and volatile material removed in vacuo affording an orange brown solid. This was purified chromatographically using silica-gel as the stationary phase and a 1:1 mixture of 40°–60° petroleum ether and diethyl ether as eluent. The product thus obtained was recrystallised from petroleum ether 80°–100° C. affording (0.8 g) of the sub-title compound. M.P. 165°–168° C.

(e)
6-Methyl-4-oxo-10-propyl-4H-pyrano[3,2-g]quinoline-2,8-dicarboxylic acid

To a stirred solution of the product of step (d) (0.9472 g) in ethanol (200 mls) on a steam bath was added 0.105 M NaOH (48.8 mls). Heating was continued for 1.5 hours. The mixture was then filtered and volatile material removed under reduced pressure. The resulting oil was dissolved in distilled water (50 mls) and excess acetone was added resulting in precipitation of the bissodium salt. The salt was dissolved in water, acidified and extracted into ethyl acetate, dried using magnesium sulphate, filtered and the volatile material removed under reduced pressure affording 0.3 g of pure sub-title compound. M.P. 252°–254° C.

(f) Disodium
6-methyl-4-oxo-10-propyl-4H-pyrano[3,2-g]quinoline-2,8-dicarboxylate The product of step (d) (1.0 gm) was converted to 0.75 g of the title compound by the process of Example 3(g).

Analysis: Found: C, 52.4; H, 3.9; N, 3.4%. $C_{18}H_{13}NNa_2O_6$ 1.5 moles $H_2O$ (6.6%) Requires: C, 52.4; H, 3.9; N, 3.4%.

NMR Spectroscopy also confirms formation of the title compound.

EXAMPLE 8

4,6-Dioxo-10-propyl-4H,6H-pyrano[3,2-g]quinoline-3,8-dicarboxylic acid (a) Diethyl
4,6-dioxo-10-propyl-4H,6H-pyrano[3,2-g]quinoline-3,8-dicarboxylate A mixture of ethyl 7-amino-4-oxo-S-propyl-4H-1-benzopyran-2-carboxylate (1.5 g, 0.00545 mole) diethyl ethoxymethylenemalonate (1.17 g, 1.1 ml, 0.00545 mole) and dry toluene (20 ml) was stirred and heated on a steam bath for 16 hours. A further aliquot of diethyl ethoxymethylenemalonate (0.5 ml) was added and the mixture was heated at reflux for 20 hours. Volatile components were removed by evaporation and the residue was added over 5 minutes to preheated diphenyl ether (40 ml) at 25° C. This mixture was heated at reflux for 1 hour, allowed to cool, and poured into 40°-60° petroleum ether. Insoluble material was filtered off, washed with 40°-60° petroleum ether, boiled with ether and crystallised from ethanol to give the sub-title compound as a pale brown solid (0.38 g) mp 232°-4°.

(b) 4,6-Dioxo-10-propyl-4H,6H-pyrano[3,2-g]quinoline-3,8-dicarboxylic acid

A solution of the product of step (a) (2.95 g, 0.0074 mole) and 47% aqueous hydrobromic acid (25 ml) in glacial acetic acid (100 ml) was heated at reflux for 6 hours, them allowed to cool to give the required sub-title product in 2 crops as a buff solid (2.29 g), which was rigorously dried in vacuo to remove residual acetic acid. NMR and mass spectroscopy confirmed the structure of the product.

(c) Disodium 4,6-dioxo-10-propyl-4H,6H-pyrano[3,2-g]quinoline-2,7-dicarboxylate The diacid product from step (b) (1.5 g, 0.00437 mole) was converted to the disodium salt, as a buff powder (1,22 g), by the process of Example 1(c).

Analysis: Found: C 50.0%; H 3.7%; N 3.2%. $C_{17}H_{11}NNa_2O_7$ 5.1% $H_2O$ Requires: C 50.0%; H 3.3%; N 3.4%.

EXAMPLE 9

Disodium 6-chloro-4-oxo-7,10-dipropyl-4H-pyrano[3,2-g]quinoline-2,8-dicarboxylic

(a) Diethyl 4,6-dioxo-10-propyl-4H,6H-pyrano[3,2-g]quinoline-2,8-dicarboxylate 4,6-Dioxo-10-propyl-4H,6H-pyrano[3,2-g]quinoline-2,8-dicarboxylic acid (3.9 g) was converted to 3.0 g of the sub-title compound as a yellow powder, mp 211°-213° C., using the process of Example 6(a) and ethanol.

(b) Diethyl 4-oxo-6-(prop-2-enyloxy)-10-propyl-4H-pyrano[3,2-g]quinoline-2,8-dicarboxylate The product of step (a) (3.0 g), anhydrous potassium carbonate (1.6 g) and allyl bromide (1.26 g; 0.902 mls) in dry dimethylformamide were stirred for 17 hours. The reaction mixture was poured into water and the precipitated product collected by filtration and dried to give 3.0 g of pale yellow product, mp 151°-153° C.

(c) Diethyl 4,6-dioxo-7-(2-propenyl)-10-propyl-4H,6H-pyrano[3,2-g]quinoline-2,8-dicarboxylate The product of step (b) (0.5 g) in diethylanilino (5 mls) was refluxed for 1½ hours. The reaction mixture was cooled, poured into 60°-80° petroleum ether and the precipitated product was collected by filtration, washed well with petroleum ether and dried. A recrystallisation from ethanol gave 0.14 g of yellow crystals, mp 137°-139° C.

(d) Diethyl 4,6-dioxo-7,10-dipropyl-4H,6H-pyrano[3,2-g]quinoline-2,8-dicarboxylate The product of step (c) (0.5 g) was dissolved in ethanol (50 mls), treated with 5% Pd/C (0.1 g) and hydrogenated at 3 atmospheres pressure until hydrogen uptake had ceased. The reaction mixture was filtered, and the filtrate was evaporated to dryness to give 0.4 g of the desired product. A recrystallisation from aqueous ethanol gave material having mp 127°-130° C.

(e) Diethyl 6-chloro-4-oxo-7,10-dipropyl-4H-pyrano[3,2-g]quinoline-2,8-dicarboxylate The product of step (d) (1.8 g) in dry benzene (100 mls) was treated with phosphorous oxychloride (1.12 mls) and refluxed for 6 hours. The reaction mixture was cooled, treated with ethyl acetate, and washed well with water. The organic layer was separated, dried, and the solvent evaporated to leave 1.7 g of residue. A recrystallisation from 60°-80° petroleum ether gave 1.16 g of the desired product, mp 145°-147° C.

(f) 6-Chloro-4-oxo-7,10-dipropyl-4H-pyrano[3,2-g]quinoline-2,8-dicarboxylic acid 0.1 N Sodium hydroxide (28.9 mls) was added dropwise to the diester product of step (e) (0.646 g) in refluxing methanol (100 mls) with stirring, over 15 minutes. The reaction mixture was refluxed and stirred for a further 3 hours and the solution filtered and evaporated. The residue was dissolved in water (100 mls) and acidified. The precipitated acid was collected by filtration, washed with water and dried to give 0.4 g of the desired product. A recrystallisation from ethyl acetate gave 0.24 g, mp 204° (dec).

(g) Disodium 6-chloro-4-oxo-7,10-dipropyl-4H-pyrano[3,2-g]quinoline-2,8-dicarboxylate The product of step (f) was converted to 0.668 g of the desired product by the process of Example 3(g).

Analysis: Found: C, 49.03; H, 4.27; N, 2.96; Cl, 7.24%. $C_{20}H_{16}ClNNa_2O_6$ 8.53% water. requires: C, 49.03; H, 4.22; N, 2.86; Cl, 7.25%.

The products of steps (b), (c) and (d) may be hydrolysed to the free acids.

EXAMPLE 10

7-Chloro-5-methoxy-4-oxo-4H-pyrano[3,2-h]-quinoline-2,9-dicarboxylic acid

(a) N-(3-Acetyl-2-hydroxy-4-methoxyphenyl)acetamide 1-(3-Amino-2-hydroxy-6-methoxy-phenyl)ethanone (12.9 g) was added to a mixture of acetic acid (3 mls) and water (20 mls) and heated to 60° C. Acetic anhydride (9.5 mls) was then added and the whole heated on a steam bath for thirty minutes. The reaction mixture was poured into water and extracted into ether, which was dried using magnesium sulphate, and after filtration the volatiles were removed in vacuo, affording a golden brown solid which was triturated with chloroform and dried under reduced pressure, yielding 3.7 g of the sub title compound, mp 160°-162° C.

(b) Ethyl 8-amino-6-methoxy-4-oxo-4H-1-benzopyran-2-carboxylate

Sodium (1.4 g) was reacted with ethanol (150 mls). The resultant solution was cooled and stirred vigorously, and to this solution was added a slurry of the product of step (a) (3.5 g) and diethyl oxalate (5.4 mls) in ethanol (50 mls). The mixture was heated under reflux for three hours, poured into water and the aqueous solution was extracted into ethyl acetate, which was washed with a little water and dried using magnesium sulphate. After filtration the solvent was removed in vacuo. This procedure yielded an oil to which was added concentrated hydrochloric acid (3 mls) and ethanol (100 mls). This solution was heated under reflux overnight. The volatiles were removed in vacuo, to afford the sub title compound (2.3 g). N.M.R. and Mass Spectroscopy confirmed the structure.

(c) Dimethyl (5-methoxy-2-ethoxycarbonyl-4-oxo-4H-1-benzopyran-8-yl)-amino-but-2-ene-1,4-dioate To the product of step (b) (2.3 g) was added ethanol (200 mls) and dimethyl acetylene dicarboxylate (1.3 mls). The whole was heated under reflux for twenty four hours. The volatiles were then removed in vacuo to afford a sticky yellow-orange solid which was triturated with a petroleum ether-diethyl ether mixture. The resulting solid was filtered under reduced pressure affording (1.8 gm) of the sub-title compound. N.M.R. Spectroscopy and Mass Spectroscopy confirmed the structure.

(d) Methyl 5-methoxy-2-ethoxycarbonyl-4,7-dioxo-4H,7H-pyrano[3,2-h]quinoline-9-carboxylate To refluxing diphenyl ether (50 mls) was added the product of step (c) (1.8 gm). Refluxing was continued for five minutes, and the mixture was then allowed to cool. Light petroleum ether was added and the precipitated product was filtered under reduced pressure, and washed with a little diethyl ether, affording 1.0 g of crude sub title compound. This solid was triturated with a mixture of hot ethyl acetate and chloroform, filtered under reduced pressure and dried. The material was recrystallised from toluene, and dried in vacuo at 89° C. over phosphorous pentoxide for four hours, resulting in 0.2 g of the sub-title compound, mp 260°–261° C.

(e) Ethyl 7-chloro-5-methoxy-9-methoxycarbonyl-4-oxo-4H-pyrano[3,2-h]quinoline-2-carboxylate To a stirred solution of the product of step (d) (1 gm) in dry dichloroethane was added phosphoryl chloride (1 ml) and the whole stirred at room temperature for seven hours. An addition of phosphoryl chloride (1 ml) was made and stirring was continued for a further two days. The flask's contents were cautiously poured into water, extracted into chloroform, charcoaled and dried using magnesium sulphate. A little silica gel was added to the filtrate, which was then refiltered and the volatiles were removed in vacuo affording, as an off white solid, the sub-title compound (0.4 g). N.M.R. Spectroscopy and Mass Spectroscopy confirmed the structure.

(f) 7-Chloro-5-methoxy-4-oxo-4H-pyrano[3,2-h]-quinoline-2,9-dicarboxylic acid To the product of step (e) (2.6 g) in glacial acetic acid (20 mls) was added concentrated hydrochloric acid (5.2 mls) and the whole was heated on a steam bath for three hours, during which time a solid slowly crystallised out of solution. The reaction mixture was cooled to room temperature and the crystallised solid was filtered off, washed thrice with glacial acetic acid and twice with diethyl ether. The resulting pale yellow solid was dried over sodium hydroxide pellets at 90° C. under a reduced pressure of 1 mm Hg for 2.5 hours, affording 0.8 g of the sub-title compound. N.M.R. Spectroscopy confirmed the structure.

(g) Disodium 7-chloro-5-methoxy-4-oxo-4H-pyrano[3,2-h]-quinoline-2,9-dicarboxylate The product of step (f) (0.7316 g) suspended in water was treated with sodium bicarbonate (0.45 g) and stirred until complete dissolution occurred. The solution was treated with pure acetone and cooled. The precipitated product was collected by filtration and dried under reduced pressure at 80° C. for four hours, affording (0.38 g) of the title compound.

Analysis: Found: C, 45.3; H, 2.04; N, 3.2; Cl 8.4%. $C_{15}H_6ClNa_2NO_7 5.26\%H_2O$ Requires: C, 43.3; H, 2.1; N, 3.4; Cl 8.5%.

N.M.R. Spectroscopy also confirmed the preparation of the title compound.

EXAMPLE 11

6-Chloro-4-oxo-10-(prop-2-enyl)-4H-pyrano[3,2-]-quinoline-2,8-dicarboxylic acid

(a) Ethyl 8-(prop-2-enyl)-7-amino-4-oxo-4H-benzopyran-2-carboxylate 1-(4-Acetylamino-3-(prop-2-enyl)-2-hydroxyphenyl)ethanone (20 g) and diethyl oxalate (30.95 g; 28.7 ml) were added to a previously formed solution of sodium ethoxide (by addition of sodium (9.7 g) to dry ethanol (243.4 ml) with stirring.

The reaction mixture was stirred under reflux for 3 hours, cooled and then poured into water. The precipitated product was extracted into chloroform, dried and evaporated to dryness under reduced pressure. The yellow residual solid was dissolved in fresh, dry ethanol (324.5 ml), concentrated hydrochloric acid (3.25 ml) added and the reaction mixture refluxed for 17 hours. The whole was poured into water (1.5 liter) extracted into ethyl acetate, washed with water and dried over magnesium sulphate. The solvent was evaporated to dryness and the residue triturated with 40–60 petroleum ether to give 19.6 g of brown crystalline solid. A 1.0 g sample of the crude product was recrystallised from ethanol to give a crystalline solid, mp 142.5°–143° C.

(b) Dimethyl N-(2-ethoxycarbonyl-4-oxo-8-(prop-2-enyl)-4H-1-benzoyran-7-yl)-2-aminobut-2-ene-1,4-dioate The product of step (a) (18.6 g) and dimethylacetylenedicarboxylate (11.95 g; 10.86 ml) in ethanol (148 ml) were refluxed together for 17 hours. The reaction mixture was cooled to 10° C. and the precipitate was collected by filtration, washed with a little ethanol and dried to give 15.8 g of product. A 0.9 g sample was recrystallised from ethanol to give a crystalline solid, mp 148°148.5° C.

(c) Ethyl-8-methoxycarbonyl-4,6-dioxo-10-(prop-2-enyl)-4H,6H-pyrano[3,2-q]quinoline-2-carboxylate The product of step (b) (14.0 g) was added to diphenyl ether (200 ml) under reflux with stirring. The reaction mixture was refluxed for a further 5 minutes, cooled and poured into 60–80 petroleum ether (2.0 l). The precipitated product was collected by filtration, dried and recrystallised from ethyl acetate to give 3.5 g of yellow solid.

Analysis: Found: C, 62.5%; H, 4.5%; N, 3.6%. Required for $C_{20}H_{17}NO_7$: C, 62.5%; H, 4.7%; N, 3.6%.

(d) Ethyl 6-chloro-8-methoxycarbonyl-4-oxo-10-(prop-2-enyl)-4H-pyrano[3,2-g]-quinoline-2-carboxylate The product of step (c) (2.9 g), phosphoryl chloride (2.33 g; 1.4 ml) and dry dichloromethane (174.1 m) were refluxed for 6 hours. The reaction mixture was allowed to cool and then evaporated to dryness under reduced pressure. The crude product was eluted down a silica gel column using chloroform-ethyl acetate (15:1) as eluant, and then recrystallised from ethyl acetate to give 1.12 grams of product as dark-yellow needles, mp 197°–198° C.

(e) Disodium 6-chloro-4-oxo-10-(prop-2-enyl)-4H-pyrano[3,2-g]quinoline-2,8-dicarboxylate 0.1 m sodium hydroxide solution (24.9 ml) was added dropwise to the product of step (d) (0.5 grams) in refluxing pure methanol (100 ml), with stirring. The whole was refluxed for a further 10 minutes after addition, the methanol was removed under reduced pressure and the title compound obtained by precipitation by the addition of acetone. The product was collected by filtration and dried in vacuo at 60° C. to give 0.37 grams of dark yellow solid.

Analysis: Found: C 48.53%; H 2.44%; N 3.04%; Cl 8.4%. Rqd for $C_{17}H_{18}ClNNa_2O_6$ 3.99% $H_2O$: C 48.59%; H 2.34%; N 3.3%; Cl 8.7%.

NMR Spectroscopy also confirms the presence of the title compound.

EXAMPLE 12

4-Chloro-10-oxo-10H-pyrano[2,3-h]quinoline-2,8-dicarboxylic acid

(a) Ethyl 5-amino-4-oxo-4H-benzopyran-2-carboxylate

Ethyl 5-nitro-4-oxo-4H-benzopyran-2-carboxylate (10 g, 38.022 mmoles) in ethanol (250 mls) was added to 5% Pd/C (1 g) in ethanol (50 ml) in a hydrogenation vessel. Two drops of concentrated hydrochloric acid were then added to the above mixture. The mixture was then hydrogenated at 3 atmospheres pressure at room temperature for 2 hours. The catalyst was then filtered off through a filter aid which was washed with chloroform. The filtrate was evaporated to give a yellow solid (8.1 g, 91.5%). NMR and mass spectra confirmed that the desired compound had been made.

(b) 8-Ethoxycarbonyl-2-methoxy carbonyl-4,10-dioxo-4H,10H-pyrano[2,3-h]-quinoline The product of step (a) (6.1 g, 26.18 mmole) and dimethyl acetylene-dicarboxylate (11 g; 77.46 mmoles) were heated in ethanol (180 ml) for 7 hours. The reaction mixture was cooled and was diluted with water. Half of the original volume of ethanol was removed and the concentrated mixture was extracted with ethyl acetate. The organic layer was washed with a large volume of water, dried and evaporated to give a yellow solid (8.5 g, 86%).

The solid (8.5 g, 22.66 mmole) was added slowly to preheated diphenyl ether (90 ml, 240° C.) under $N_2$ with stirring. After addition the mixture was brought to reflux for 15 minutes. The mixture was cooled and poured into petroleum ether (40°–60° C., 200 ml) to give the subtitle product as a light grey solid (4 g, 51.3%) mp=166°–70° C.

(c) 8-Ethoxycarbonyl-4-chloro-2-methoxycarbonyl-10-oxo-10H-pyrano[2,3-h]quinoline The product of step (b) (1.3 g, 3.79 mmole) and phosporyl chloride (0.69 ml) in dry dichloroethane (80 ml) were heated to reflux for 15 minutes. The reaction mixture was then cooled and treated with water. The mixture was extracted with dichloroethane, the organic layer was washed with water, dried, and evaporated to give a brown solid. This was dried in vacuo over $P_2O_5$ at 50° C. to give the sub-title compound (0.9 g; 66%).

Analysis: Found: C, =55.8; H, =3.6; N, =3.4. Required for 1.1% $H_2O$: C, =55.8; H, =3.4; N, =3.6%.

(d) Disodium 4-chloro-10-oxo-10H-pyrano[2,3-h]quinoline-2,8-dicarboxylate

Sodium hydroxide (0.1 N, 16.4 ml) was added slowly to a boiling solution of the product of step (c) (1.3 g, 3.6 mmole) in methanol. After the addition, the mixture was left to reflux for a further 15 minutes. The mixture was cooled and added to a large volume of acetone, to give a fine pink precipitate. This was filtered off and the resulting solid was recrystallised from water to give the subtitle compound as a pale pink solid (0.6 g; 46%).

Theoretical for 9.75% $H_2O$: C, 40.8; H, 2.48; N, 2.75; Cl, 7.3. Found: C, 40.4; H, 2.75; N, 2.7; Cl, 7.2%.

EXAMPLE 13

N-(2-Hydroxy-2-[4-hydroxy-3-hydroxymethylphenyl]ethyl)-1,1-dimethylethylammonium sodium 6-chloro-4-oxo-10-propyl-4H-pyrano[3,2-g]quinoline-2,8-dicarboxylate N-(2-Hydroxy-2-[4-hydroxy-3-hydroxymethylphenyl]ethyl)-1,1-dimethylamine (0.284 g), pure sodium bicarbonate (0.0997 g) and 6-chloro-4-oxo-10-propyl-4H-pyrano[3,2-g]quinoline-2,8-dicarboxylic acid containing 5.2% water (0.452 g) were combined in pharmaceutically pure water (20 ml), and stirred until complete solution was obtained. The solution was filtered and freeze dried to afford the title compound as a yellow solid (0.6 g).

Analysis: Found: C 54.27%; H 5.72%; N 4.63%; Cl 6.0%. $C_{30}H_{32}ClN_2NaO_9$.6.4%$H_2O$ requires: C 54.3%; H 5.27%; N 4.22%; Cl 5.4%.

EXAMPLE 14

Calcium 6-chloro-4-oxo-10-propyl-4H-pyrano[3,2-g]quinoline-2,8-dicarboxylate Disodium 6-chloro-4-oxo-10-propyl-4H-pyrano[3,2-g]quinoline-2,8-dicarboxylate (0.5 g) was dissolved in water (1 ml) and a solution of anhydrous calcium nitrate (0.05 g) in methanol (5 ml) was added. After stirring for one hour the precipitate was collected and washed well with water. Drying in vacuo at 50° C. afforded the title compound (0.27 g) as a yellow solid.

Analysis: Found: C 41.57%; H 4.03%; N 3.13%; Cl 7.1%. $C_{17}H_{10}CaClNO_6.5H_2O$ requires: C 41.57%; H 4.12%; N 2.85%; Cl 7.2%.

EXAMPLE 15

6-Ethylsulphinyl (and 6-ethylsulphonyl)-4-oxo-10-propyl-4H-pyrano[3,2-g]quinoline-2,8-dicarboxylic acid (a) Ethyl 6-ethylthio-8-methoxycarbonyl-4-oxo-10-propyl-4H-pyrano[3,2-g]quinoline-2-carboxylate (0.9 g) was taken up in dichloromethane (50 ml) and treated with m-chloroperbenzoic acid (2.5 g). After stirring at room temperature for 3 days the suspended solids were removed by filtration, and the solution was washed well with saturated sodium bisulphite solution, dried and evaporated to afford a brown residue (0.68 g).

This residue was separated into its components by high pressure liquid chromatography. Two major fractions were recovered:
(i) the sulphoxide—(0.38 g)
(ii) the sulphone—(0.22 g)

The two materials were identified by NMR and mass spectrometry.

(b) Disodium 6-ethylsulphinyl-4-oxo-10-propyl-4H-pyrano[3,2-g]quinoline-2,8-dicarboxylate The product (i) of step (a) (0.36 g) was hydrolysed by the method of Example 3 (g) to afford the title compound (0.18 g).

Structure was supported by NMR and IR.

(c) Disodium 6-ethylsulphonyl-4-oxo-10-propyl-4H-pyrano[3,2-g]quinoline-2,8-dicarboxylate The product (ii) of section (a) above was hydrolysed in the same manner as in (b) above to afford the sub-title compound (0.12 g).

Structure was supported by NMR and IR.

EXAMPLE 16

2-Hydroxy-9-oxo-5-propyl-9H-pyrano[3,2-g]quinoxaline-3,7-dicarboxylic acid

(a) 1-(4-Acetylamino-2-hydroxy-5-nitro-3-propylphenyl)ethanone 1-(4-Acetylamino-2-hydroxy-3-propylphenyl)ethanone (58.75 g) was suspended in glacial acetic acid (750 ml), and this suspension was treated with a mixture of glacial acetic acid (250 ml), acetic anhydride (48 ml) and conc. nitric acid (10.2 ml) with vigorous stirring. After 18 hours the insoluble material was collected and dried in vacuo to afford the title compound 29.1 g. The structure was confirmed by NMR and mass spectrometry.

(b) Methyl 7-amino-6-nitro-4-oxo-8-propyl-4H-1-benzopyran-2-carboxylate

Sodium (11.5 g) was dissolved in ethanol (500 ml), and to it was added the product of step (a) above (28 g), and then, after 5 minutes stirring, diethyl oxalate (31.5 g) was also introduced. The reaction was heated under reflux for 3 hours, then cooled and poured into a vigorously agitated mixture of chloroform (2 liter), water (400 ml) and conc. hydrochloric acid (100 ml). The organic solution was dried and evaporated, and the residue was taken up in ethanol (400 ml) containing conc. hydrochloric acid (4 ml). The solution was heated to reflux for 4 hours, and then glacial acetic acid (100 ml), and conc. hydrochloric acid (10 ml) were added and boiling was continued for 18 hours. The ethanol was removed in vacuo, and the residue was heated in a mixture of glacial acetic acid (150 ml), conc. hydrochloric acid (200 ml) and water (150 ml) under reflux for 3 hours.

After cooling, the precipitate was collected and dried, and then suspended in dry methanol (500 ml), and this suspension was heated to reflux while hydrogen chloride gas was passed through for one hour. The solvent was removed in vacuo and the residue was taken up in ethyl acetate and dried over potassium carbonate. Removal of solvent afforded the required material, 15.1 g. Crystallisation from methanol affords a yellow solid, mp 160°–161° C.

(c) Methyl 6,7-diamino-4-oxo-8-propyl-4H-1-benzopyran-2-carboxylate

The product of step (b) above (0.5 g) was dissolved in ethyl acetate (150 ml) containing glacial acetic acid (5 ml), and the mixture was hydrogenated over 5% Pd/C (0.1 g) at 3 atmospheres pressure. The catalyst was removed by filtration through glass fibre paper under nitrogen, and solvent was removed at 40° C. and then 50° C. The residue was triturated with methylene chloride, and the insoluble solid was collected and dried to afford a brown solid (0.125 g), mp 221°–222° C. identified as the sub-title compound by NMR and MS.

(d) Ethyl 2-hydroxy-7-methoxycarbonyl-9-oxo-5-propyl-9H-pyrano[3,2-g]quinoxaline-3-carboxylate The product of step (c) above (0.6 g) was suspended in ethanol (25 ml), and diethyl ketomalonate (0.382 g) was added. The mixture was refluxed for 18 hours, and the resulting precipitate was collected (0.29 g) and identified as the sub-title compound by NMR and MS: $\delta_{DMSO}$: 1.0 (3H,t), 1.4 (3H, t), 1.6 (2H, m), 3.0 (2H, t), 4.0 (3H, s), 4.4 (2H, q), 6.95 (1H, s), 8.2 (1H, s).

M+: 386, BP 283.

(e) Disodium 2-hydroxy-9-oxo-5-propyl-9H-pyrano[3,2-g]quinoxaline-3,7-dicarboxylate The product of step (d) above (0.498 g) was suspended in stirred, refluxing methanol (200 ml), and to it was added N/10 NaOH solution (25.8 ml) dropwise. After 18 hours, the methanol was removed in vacuo and the aqueous residue was cooled in ice. The resulting precipitate was discarded. The aqueous solution was diluted with acetone (200 ml) and the precipitate which appeared was collected and dried. It was then redissolved in a little water and freeze-dried to afford a red-brown powder (0.25 g).

Analysis: $C_{16}H_{10}N_2Na_2O_7.13.44\%$ $H_2O$ Requires: C 42.85%; H 3.74%; N 6.25%. Found: C 42.85%; H 3.65%; N 5.81%.

NMR also confirms the structures of the title compound.

EXAMPLE 17

10-Chloro-1-oxo-1H-pyrano[3,2-f]quinoline-3,8-dicarboxylic acid

(a) Ethyl methyl 10-hydroxy-1-oxo-1H-pyrano[3,2-f]quinoline-3,8-dicarboxylate Ethyl 6-amino-4-oxo-4H-1-benzopyran-2-carboxylate (3.9 g; 16.7 mmole) in ethanol (70 ml) and dimethylacetylene dicarboxylate (2.84 g; 20 mmole) were heated under reflux for 2 hrs. The solution was cooled and the solvent removed on the rotary evaporator to give a green solid.

The solid was added all at once to refluxing diphenyl ether (50 ml) and heating was continued for 25 mins. The mixture was allowed to cool and then poured into a mixture of diethyl ether (25 ml) and petroleum ether (bp 40°–60°) (40 ml) and the brown solid was filtered off and recrytallised from chloroform to give the title compound as a dark green solid (2.9 g; 50.6%), mp 247°–8.5°.

(b) Ethyl methyl 10-chloro-1-oxo-1H-pyrano[3,2-f]quinoline-3,8-dicarboxylate The product of step (a) (1.35 g; 3.9 mmole) suspended in dichloroethane was treated with thionyl chloride (0.9 g; 7.5 mmole) and dimethylformamide (4 drops). The mixture was heated under reflux for 6 hrs adding more thionyl chloride (0.2 ml) after 3 hrs. The mixture was evaporated to dryness and triturated with ether to give a buff solid (1.35 g; 96%), mp 193° shown to be the title compound by its NMR and mass spectrum.

(c) 10-Chloro-1-oxo-1H-pyrano[3,2-f]quinoline-3,8-dicarboxylic acid

Ethyl methyl 10-chloro-1-oxo-1H-pyrano[3,2-f]quinoline-3,8-dicarboxylate (300 mg; 0.83 mmole) in methanol (30 ml) was heated under reflux during the dropwise addition of M/10 aqueous sodium hydroxide (16.6 ml; 1.66 mmole) with stirring over 1.5 hrs. After the addition the mixture was heated under reflux for a further 2 hrs when it was cooled and poured into dilute aqueous hydrochloric acid. The brown solid was filtered off and dried in a vacuum oven over sodium hydroxide pellets. This gave analytically pure title compound 210 mg (79%) (decomp. 253°). NNMR (d$^6$ DMSO) $\delta$, 8.48, 8.13 (AB quartet, J=9H); $\delta$, 8.33 (s,1H), 7.2 (s, 1H).

EXAMPLE 18

10-Chloro-4-oxo-4H-pyrano[2,3-f]quinoline-2,8-dicarboxylic acid

(a) Ethyl 7-amino-4-oxo-4H-1-benzopyran-2-carboxylate

A solution of sodium metal, (18.4 g, 0.8 gatom), in dry ethanol (1200 ml), was treated with N-(4-acetyl-3-hydroxyphenyl)acetamide (30.88 g, 0.16 mole). This mixture was stirred for 15 mins then diethyl oxalate (58.4 g, 54.3 ml, 0.4 mole), was added dropwise over 30 mins. The resulting mixture was heated and stirred at 60° C. for 2 hrs, allowed to cool and poured into a mixture of chloroform (600 ml), conc HCl (85 ml), and water (2000 ml). The organic layer was isolated and combined with a chloroform wash of the aqueous layer. The combined chloroform extracts were washed well with water then evaporated to dryness. The residue was taken into ethanol (400 ml), and conc.HCl (10 ml), was also added. The solution was heated at reflux for 30 minutes then evaporated to dryness. The residue was treated with ether and ethanol was added dropwise until the residue began to solidify. Insoluble material was filtered off, washed again with ether and the required sub-title product was recovered as a brown solid (20.5 g), (55%), mp 192°–194°. NMR and mass spectra confirmed the structure.

(b) Dimethyl 2-(2-ethoxycarbonyl-4-oxo-4H-1-benzoypyran-7-ylamino)but-2-ene-1,4-dioate A solution of the product of step (a) (4.2 g, 0.018 mole), and dimethylacetylenedicarboxylate, (7.68 g, 6.6 ml, 0.054 mole), in ethanol (200 ml), was heated at reflux for 3½ hrs. Solvent was evaporated off and the residue was triturated with ether. Insoluble material was filtered off and washed with ether to give the required product as a buff coloured solid (4.3 g), (64%), mp 147°–51°. NMR and mass spectra confirmed the structure.

(c) Ethyl 8-methoxycarbonyl-4,10-dioxo-4H,10H-pyrano[2,3-f]quinoline-2-carboxylate Diphenyl ether (140 ml), was heated to 240° C. and the product of step (b) (3.85 g, 0.01027 mole), was added quickly but in small portions. The resulting solution was heated at reflux for 5 minutes then allowed to cool, when a gel-like precipitate formed. This was added to a mixture of ether and 40°–60° petroleum ether and allowed to stand. Insoluble material was filtered off, washed well with ether and dried in vacuo to leave the required product as a pale brown powder (3.25 g), 92%, mp 239°–41°. The structure was confirmed by NMR and mass spectra.

(d) Ethyl 10-chloro-8-methoxycarbonyl-4-oxo-4H-pyrano[2,3-f]quinoline-2-carboxylate A mixture of ethyl 8-methoxycarbonyl-4,10-dioxo-4H,10H-pyrano[2,3-f]quinoline-2-carboxylate, (2.0 g, 0.00583 mole), phosphoryl chloride, (1.1 ml, 1.8 g, 0.01166 mole) and dry 1,2-dichloroethane, (500 ml), was heated at reflux for 2½ hours. The resulting solution was allowed to cool, was filtered, and the filtrate was evaporated to dryness. The residue was triturated with ether and dried to leave the required sub-title material as an off-white fluffy solid, (1.1 g), mp 209°, (52%). The structure was confirmed by NMR and mass spectra.

(e) Disodium 10-chloro-4-oxo-4H-pyrano[2,3-f]quinoline-2,8-dicarboxylate

The diester product of step (d) above was hydrolysed by the method of Example 11 (e) to afford the title compound. The structure was confirmed by nmr and elemental analysis:

Found: Cl, 8.57%; C, 41.12%; H, 2.46%; N, 3.19%. $C_{14}ClNNa_2O_6.2\frac{1}{2}H_2O$ requires: Cl, 3.67%; C, 41.14%; H, 2.22%; N, 3.43%.

EXAMPLE 19

Disodium 4-oxo-10-propyl-4H-pyrano[3,2-g]quinoline-2,8-dicarboxylate

(a) Methyl 6-acetyl-7-hydroxy-8-propylquinoline-2-carboxylate

Methyl 6-acetyl-4-ethylthio-7-hydroxy-8-propyl-quinoline-2-carboxylate (1.0 g), was added to Raney Nickel (16 g wet wt; previously washed with ethanol) in dry ethanol (100 mls), and reflux for 1½ hours. The catalyst was filtered off, and the filtrate evaporated to dryness. The residue was triturated with 40°–60° petroleum ether and the yellow solid collected by filtration to give 0.6 g of the sub-title product. A recrystallisation from ethanol gave 0.2 g, mp 110°–111°.

(b) Diethyl 4-oxo-10-propyl-4H-pyrano[3,2-g]quinoline-2,8-dicarboxylate

The product of step (a) (1.75 g), and diethyl oxalate (4.38 g) dissolved in dry ethanol (50 mls) was added to sodium ethoxide solution (prepared by the addition of sodium (0.35 g), to dry ethanol (50 mls) with stirring. The reaction mixture was stirred under reflux for 1 hr, cooled, poured into ethyl acetate and dilute hydrochloric acid and the organic layer separated, washed well with water and dried. The solvent was evaporated and the residue treated with ethanol saturated with hydrogen chloride gas (100 mls) and refluxed for 10 mins. The reaction mixture was cooled, poured into water, and the precipitated product collected by filtration, washed well with water and dried to give 2.5 g of product. A recrystallisation from ethanol gave 1.25 g, mp 168°–171°.

(c) 4-Oxo-10-propyl-4H-pyrano[3,2-g]quinoline-2,8-dicarboxylic acid

The product of step (b) (1.118 g) was suspended in methanol (100 mls) and heated and stirred under reflux with the dropwise addition of N/10 sodium hydroxide solution (58.37 mls). The reaction mixture was stirred and heated under reflux for a further 15 mins, cooled, filtered and acidified. The precipitated product was collected by filtration, washed with water and dried to give 0.852 g, mp 252° dec.

(d) Disodium 4-oxo-10-propyl-4H-pyrano[3,2-g]quinoline-2,8-dicarboxylate

The product of step (c) (hemihydrate 0.629 g) and sodium bicarbonate (0.3145 g) were stirred in water (70 mls) until a complete solution was formed. The solution was filtered and the filtrate freeze dried to give 0.658 g of the desired salt.

Analysis: Found: C; 48.3%; H; 4.1%; N; 3.05%. $C_{17}H_{11}NNa_2O_6 3H_2O$ Required: C; 48.0%; H; 4.0%; N; 3.29%.

EXAMPLE 20

4-Oxo-6-phenoxy-10-propyl-4H-pyrano[3,2-g]quinoline-2,8-dicarboxylic acid

(a) Methyl 6-acetyl-7-hydroxy-4-phenoxy-8-propyl-quinoline-2-carboxylate

Phenol (10.0 g) which had been crushed in a mortar and pestle, was added to crushed potassium hydroxide (0.36 g) in a flask which was immersed in an oil bath. This was stirred at 60°–65° C. for 5 minutes before methyl 6-acetyl-4-chloro-7-hydroxy-8-propyl-quinoline-2-carboxylate (1.0 g) was added. The whole was stirred at 60°–65° C. for 1.5 hours and the phenol was then removed by steam distillation.

The required product was separated from the residual mixture by filtration and dried, yielding 0.81 g of the sub-title compound as yellow crystals, mp 195°–196° C.

(b) Diethyl 4-oxo-6-phenoxy-10-propyl-4H-pyrano[3,2-g]quinoline-2,8-dicarboxylate Sodium (0.25 g) was dissolved with stirring in dry ethanol (50 cm³) and when solution had been achieved, the product of step (a) (1.0 g) was added, with diethyl oxalate (2.69 g) and dry ethanol (30 cm³).

The whole was stirred at room temperature for 1 hour and then refluxed for 1.5 hours. The reaction mixture was poured into cold water and acidified with glacial acetic acid to pH 5. The product was extracted into ethyl acetate which was washed with water and dried. The solvent was removed by evaporation to give a red oil which was dissolved in dioxan (50 mls) and anhydrous hydrogen chloride bubbled through for 15 minutes. The whole was poured into ethyl acetate, washed with water and sodium bicarbonate solution and dried. The solvent was removed by evaporation to leave a dark red oil. This was crystallised from 40°–60° petroleum ether and dried to yield 0.6 g of the crude sub-title compound. This was recrystallised from ethanol to yield 0.2 g of the sub-title compound, of mp 173°–178° C. (partially melts at 161° C.).

(c) Disodium 4-oxo-6-phenoxy-10-propyl-4H-pyrano[3,2-g]quinoline-2,8-dicarboxylate The product of step (b) (0.4162 g) was stirred in methanol (50 cm³) under reflux and was treated with 0.1 N sodium hydroxide solution (17.5 cm³), dropwise. The whole was stirred and refluxed for 15 minutes after addition, cooled, filtered and the filtrate evaporated to dryness. Water (30 cm³) was added and the solution was treated with acetone until complete precipitation was attained. The product was collected by filtration and dried to give 0.22 g of the title compound.

Analysis: Found: C, 55.85%; H, 3.8%; N, 2.69%. $C_{23}H_{15}NNa_2O_7$ 6.3% $H_2O$. Requires: C, 55.85%; H, 3.7%; N, 2.8%.

NMR spectroscopy also confirms the presence of the title compound.

EXAMPLE 21

N,N'-Diphenyl-6-chloro-4-oxo-10-propyl-4H-pyrano[3,2-g]quinoline-2,8-dicarboxamide A slurry of disodium 6-chloro-4-oxo-10-propyl-4H-[3,2-g]pyranoquinoline-2,8-dicarboxylate (3 g) in 1,2- dichloroethane (80 ml) was stirred and treated dropwise with concentrated sulphuric acid (0.5 ml). Thionyl chloride (15 ml) was then added, followed by N,N-dimethylformamide (2 drops). This mixture was heated under reflux for 3.5 hours, then the solution was decanted from the sulphate salt and was evaporated. The residue was redissolved in 1,2-dichloroethane (30 ml) and added to a stirred solution of aniline (20 g) in 1,2-dichloroethane (80 ml). This mixture was allowed to stand for 0.5 hours, then the precipitated material was filtered off and washed with 40°–60° petroleum ether. Solvent traces were removed in vacuo at 50° and the remaining powder was thoroughly triturated with water, then again dried in vacuo at 50° to leave the title material as a yellow powder (2.65 g), mp >315°. Satisfactory nuclear magnetic resonance and mass spectroscopic data were obtained.

EXAMPLE 22

1,10-Dioxo-1H,10H-thiopyrano[3,2-f]quinoline-3,8-dicarboxylic acid

(a) Ethyl 6-amino-4-oxo-4H-1-benzothiopyran-2-carboxylate hydrochloride

4-Acetamidothiophenol (16.7 g) was added to a solution of potassium hydroxide (16.8 g), and acetylene dicarboxylic acid mono potassium salt (16.76 g) in water (200 ml). The mixture was heated under reflux for 2 hours, then cooled and the solution was washed twice with ethyl acetate. The mixture was treated with conc. hydrochloric acid (35 ml), and extracted into ethyl acetate. Drying and evaporation afforded a yellow solid (7 g) which was suspended in vigorously stirred tetraphosphoric acid (50 ml) heated on a steam bath. After one hour the reaction mixture was poured onto a large volume of ice-water and the precipitate was collected. The precipitate was dissolved in saturated sodium bicarbonate solution, filtered and reacidifed. The suspension formed was filtered and the solid product was dried under vacuum, and then suspended in dry ethanol (100 ml). The suspension was saturated with hydrogen chloride gas whilst being heated under reflux for 1 hour. On cooling a precipitate was formed which was collected and air dried to afford the sub-title material (1.2 g) as a grey powder. The structure was confirmed by NMR spectroscopy.

(b) 1,10-Dioxo-1H,10H-thiopyrano[3,2-f]quinoline-3,8-dicarboxylic acid methyl ethyl and diethyl esters The amine hydrochloride product of step (a) (0.71 g) was suspended in ethanol (25 ml) and treated with sodium bicarbonate (21 mg), dimethyl acetylene dicarboxylate (DMAD) (0.355 g) and triethylamine (2 drops). The mixture was heated under reflux for 18 hours, then more DMAD (0.2 ml) was added. After another 3 hours at reflux the mixture was cooled, poured into chloroform (100 ml) and washed well with water. The organic layer was dried and evaporated. Repeated extraction of the residue with hot 100°/120° petroleum ether afforded a yellow-orange oil (1.3 g).

Part of this oil (1 g) was dissolved in a little diphenyl ether and this solution was added to refluxing diphenyl ether (20 ml). After five minutes the mixture was chilled and diluted with a large volume of 60°/80° petroleum ether. A precipitate which appeared was collected and boiled with 100°/120° petroleum ether. The solid residue was recrystallised from acetonitrile to afford a fluffy yellow solid 0.23 g.

NMR and mass spectroscopy confirmed the material as a mixture of the methyl ethyl, and diethyl esters in the ratio 7:2.

(c) Disodium 1,10-dioxo-7H,10H-thiopyrano[3,2-f]quinoline-3,8-dicarboxylate

The mixed ester product of step (b) was suspended in dry methanol (50 ml) and heated under reflux with vigorous stirring while N/10 NaOH solution (10.5 ml) was added dropwise. Heating was continued for 30 minutes after addition, then the mixture was cooled, filtered and evaporated. Water (20 ml) was added to dissolve any residue and then a large volume of acetone was added to form a precipitate. The solid was collected by filtration through glassfibre filters, and immediately redissolved in a minimum of water and freeze dried.

The sub-title compound was obtained (150 mg).
Found: C, 41.05; H, 2.47; N, 3.77%. $C_{14}H_5NNa_2O_6S.11.9H_2O$ requires: C, 41.01; H, 2.6; N, 3.4%.

EXAMPLE 23

4-Oxo-10-propyl-6-(1-pyrrolidino)-4H-pyrano[3,2-g]quinoline-2,8-dicarboxylic acid

(a) 6-Acetyl-7-hydroxy-4-(1-pyrrolidino)-8-propyl-quinoline-2-carboxylic acid This material was made by the method of Example 3(d), and its structure was confirmed by NMR and mass spectroscopy.

(b) Ethyl 6-acetyl-7-hydroxy-4-(1-pyrrolidino)-8-propyl-quinoline-2-carboxylate The product of step (a) was converted to its ethyl ester by the method of Example 3e, and identified by NMR.

(c) Diethyl 4-oxo-10-propyl-6-(1-pyrrolidino)-4H-pyran[3,2-g]quinoline-2,8-dicarboxylate The product of step (b) was converted to the sub-title compound by the method of Example 3(f), and identified by NMR and ms.

(d) Disodium 4-oxo-10-propyl-6-(1-pyrrolidino)-4H-pyran[3,2-g]quinoline-2,8-dicarboxylate The product of step (c) was converted to the sub-title compound by the method of Example 3(g). The structure was confirmed by NMR and ms. $\delta_{DMSO}$ 0.9 (3H,t), 1.6 (4H,m), 1.8 (2H,m), 2.8 (4H,m), 3.6 (2H,t), 7.3 (1H,s), 7.5 (1H,s), 8.7 (1H,s).

EXAMPLE 24

10-Chloro-1-oxo-1H-thiopyrano[3,2-f]quinoline-3,8-dicarboxylic acid

(a) Ethyl 10-chloro-8-methoxycarbonyl-1-oxo-1H-thiopyrano[3,2-f]quinoline-3-carboxylate Ethyl 8-methoxycarbonyl-1,10-dioxo-1H,10H-thiopyrano[3,2-f]quinoline-3-carboxylate (0.3 g), thionyl chloride (0.19 g) and dry dimethyl formamide (one drop) were heated under reflux in dry dichloroethane (25 ml) for 2½ hours, and then more thionyl chloride (0.2 ml) was introduced. The reaction was left at room temperature for 72 hours, and then refluxed for 3 hours. Solvent was removed in vacuo, and the residue was chromatographed over silica using chloroform as eluant. The sub-title material was obtained as a brown solid (0.13 g) identified by NMR and mass spectroscopy.

(b) Disodium 10-chloro-1-oxo-1H-thiopyrano[3,2-f]quinoline-3,8-dicarboxylate

The diester product of step (a) was hydrolysed by the method of Example 22(c).

The product was obtained as a yellow solid (0.095 g). Found: C, 37.46; H, 2.72; N, 2.03%. $C_{14}H_4ClNNa_2O_5S.15.4\%\ H_2O$ requires: C, 37.46; H, 3.12; N, 2.6%.

EXAMPLE 25

N,N'-Di-5-tetrazolyl-6-chloro-4-oxo-10-propyl-4H-[3,2-g]pyranoquinoline-2,8-dicarboxamide (a)

N,N'-Di-5-tetrazolyl-6-chloro-4-oxo-10-propyl-4H-[3,2-g]pyranoquinoline-2,8-dicarboxamide, disodium salt A slurry of disodium 6-chloro-4-oxo-10-propyl-4H-[3,2-g]pyranoquinoline-2,8-dicarboxylate (3 g) in 1,2-dichloroethane (80 ml) was stirred and treated dropwise with concentrated sulphuric acid (0.5 ml). Thionyl chloride (15 ml) was added, followed by N,N-dimethylformamide (2 drops). This mixture was heated under reflux for 3.5 hours and then it was evaporated to dryness. More 1,2-dichloroethane (50 ml) was added and the resulting slurry was poured into a stirred mixture of 1,2-dichloroethane (20 ml), dry pyridine (20 ml) and 5-aminotetrazole monohydrate (2.1 g). This mixture was heated on a steam bath for 16 hours and then it was evaporated. The residue was triturated with diethyl ether then with ice cold 0.01 N hydrochloric acid and with water. The insoluble material was subsequently slurried with water (15 ml) and treated with solid sodium bicarbonate (0.55 g). An almost complete solution was formed, which was filtered and then treated with acetone (~40 ml). A precipitate was deposited, which was filtered off, rinsed with acetone, dried in vacuo at 70° and recovered as a green/yellow powder, (0.7 g). NMR spectroscopy was satisfactory for the title material.

(b)

N,N'-Di-5-tetrazolyl-6-chloro-4-oxo-10-propyl-4H-[3,2-g]pyranoquinoline-2,8-dicarboxamide The product of step (a) was dissolved in water (10 ml) and the solution was acidified with a few drops of 0.1 N hydrochloric acid. A precipitate was obtained, which was filtered off, washed with water, dried crushed and recovered as a khaki powder, (0.09 g), m.p. >310°.

EXAMPLE 26

6-Chloro-10-methyl-4-oxo-4H-pyrano[3,2-g]quinoline-2,8-dicarboxylic acid (a)

2-(2-Carboxy-8-methyl-4-oxo-4H-quinolin-7-yloxy)but-2-en-1,4-dioic acid

Dimethyl acetylenedicarboxylate (12.3 ml) was added dropwise to 3-amino-2-methylphenol (12.4 g) in ethanol (100 ml), at room temperature. After 0.5 hours, N-benzyltrimethylammonium hydroxide (0.5 ml), and dimethyl acetylenedicarboxylate (12.3 ml) were added, and the reaction mixture was refluxed for 4 hours. The solution was cooled, poured into chloroform (500 ml) and washed with water (5×200 ml). The chloroform layer was dried over magnesium sulphate, and concentrated in vacuo to give a dark oil, to which was added polyphosphoric acid (70 g). The whole was stirred on a steam bath for 0.5 hours then poured onto ice, and extracted with ethyl acetate (2×200 ml). The organic extracts were combined, dried over magnesium sulphate, and concentrated in vacuo to give a dark oil (27.4 g). This oil was dissolved in ethanol (200 ml) which contained sodium hydroxide (12 g) in water (100 ml), and refluxed for 5 hours. The clear solution was cooled, the ethanol removed by distillation in vacuo, and the residue was acidified with 5 N hydrochloric acid, to give, on standing overnight, the sub-title compound (12.7 g). NMR and i.r. spectra were consistent with the proposed structure.

(b)

10-Methyl-4,6-dioxo-4H,6-pyrano[3,2-g]quinoline-2,8-dicarboxylic acid

The product of step (a) above (5.8 g; 17.4 mmole) was added portionwise to chlorosulphonic acid (20 ml) with stirring while cooling in an ice bath. The mixture was allowed to warm to room temperature and stirred for 1 hour, when it was added dropwise to a mixture of ice and water with rapid stirring. The brown solid was filtered off and recrystallised from dimethylformamide to yield a light brown crystalline solid (2.82 g; 51%) containing 1 molar equivalent of dimethylformamide of crystallisation, m.p. 302°.

(c)

6-Chloro-10-methyl-4-oxo-4H-pyrano[3,2-g]quinoline-2,8-dicarboxylic acid

The product of step (b) (315 mg; 1 mmole) was suspended in calcium chloride dried 1,2-dichloroethane (40 ml) and thionyl chloride (714 mg; 0.44 ml; 6 mmole) was added. The mixture was heated under reflux for 5 hours when the solvent and excess thionyl chloride were removed on the rotary evaporator. The residual brown solid was dissolved in acetone (50 ml) and water (5 ml) was added. The solution was heated on a steam bath for 10 mins and cooled allowing the crystallisation of a light brown solid which was filtered off and dried in a vacuum oven to give the title compound as a brown solid m.p. 320° (decomp).

EXAMPLE 27

6-Ethylamino-4-oxo-10-propyl-4H-pyrano[3,2-g]quinoline-2,8-dicarboxylic acid (a) 6-Acetyl-4-ethylamino-7-hydroxy-8-propylquinoline-2-carboxylic acid Methyl 6-acetyl-4-chloro-7-hydroxy-8-propylquinoline-2-carboxylate (8.9 g; 27.7258 mmole) and ethylamine in ethanol (33% w/w; 24 ml) was heated at 100° C. under pressure (autoclaved) for 28 hours. The mixture was cooled, treated with water and concentrated, followed by extraction with chloroform. The organic extract was washed with water, dried and evaporated to give a red solid (8.1 g; 81%).

NMR and mass spectra were consistent with the required structure.

The above intermediate (8.1 g; 21.8918 mmoles) in 70% sulphuric acid (360 ml) was heated on a steambath for 2 hours. The mixture was cooled in an icebath. The pH of the mixture was adjusted to about 7. The mixture was extracted into ethyl acetate. The organic extract was dried and evaporated to give yellow solid (6.5 g; 94%). NMR and mass spectra were consistent with the required structure.

(b) Ethyl 6-acetyl-4-ethylamino-7-hydroxy-8-propylquinoline-2-carboxylate

The product of step (a) in ethanol was saturated with hydrogen chloride gas and, when the heat of solvation subsided, the brown solution was heated to reflux on a steambath for 5 hours. The mixture was cooled and was treated with water, then concentrated and the pH of the mixture was adjusted to about 7 before extracting into ethyl acetate. The extract was washed with water, dried and evaporated to give a yellowish solid (6.2 g; 82%). NMR and mass spectra were consistent with the required structure.

(c) Diethyl 6-ethylamino-4-oxo-10-propyl-4H-pyrano[3,2-g]quinoline-2,8-dicarboxylate A mixture of the product of step (b) (2.2 g; 6.3953 mmoles) and diethyl oxalate (8.5 g; 58.2191 mole) in dry dimethylformamide (50 ml) was added slowly to a stirred suspension of ether washed sodium hydride (0.38 g, 15.83 mmole) under nitrogen. After the addition, the mixture was allowed to stir under nitrogen for 72 hours. The mixture was poured onto ice, followed by acidification with dilute hydrochloric acid. The pH of the mixture was adjusted to about 7 before extraction into ethyl acetate. The extract was washed with water, dried and evaporated to give a light yellow solid. The solid was dissolved in ethanolic hydrochloric acid and heated to reflux on a steambath for 3 hours. The mixture was cooled, and treated with water. This was then concentrated and the pH of the mixture was adjusted to about 7, followed by extraction with ethyl acetate. The extract was washed, dried and evaporated to give a brown solid (2 g; 74%). The solid was recrystallised from ethanol to give a light brown solid (1.5 g).

Elemental analysis: Theoretical: C, 64.77; H, 6.15; N, 6.57%. Found: C, 65.00; H, 6.48; N, 6.31%.

(d) Disodium 6-ethylamino-4-oxo-10-propyl-4H-pyrano[3,2-g]quinoline-2,8-dicarboxylate The product of step (c) was hydrolysed to the disodium salt by the method of Example 3 (g) to afford a cream solid.

NMR $\delta_{DMSO}$: 1.0 (3Ht), 1.3 (3H,t), 1.85 (2H,m), 3.7 (2H,t), 4.6 (2H, q), 7.15 (7H,s), 8.2 (7H,s), 9.1 (7H,s).

EXAMPLE 28

6-Dimethylamino-4-oxo-10-propyl-4H-pyrano[3,2-g]quinoline-2,8-dicarboxylic acid (a) 6-Acetyl-7-hydroxy-4-dimethylamino-8-propyl-quinoline-2-carboxylic acid Methyl 6-acetyl-4-chloro-7-hydroxy-8-propyl-quinoline-2-carboxylate (6 g; 18.6474 mmole) in 33% w/w dimethylamine in methanol (50 ml) was heated at 100° C. under pressure (autoclaved) for 24 hours. The mixture was cooled, and treated with water, concentrated, and extracted with chloroform. The extract was washed with water, dried and evaporated to give a brown solid. The solid was heated in 70% sulphuric acid (150 ml) on a steambath for 6 hours. The mixture was cooled and the pH adjusted to about 7 before extraction into chloroform. The extract was dried and evaporated to give a yellow solid (1.25 g). NMR and mass spectra were consistent with the required structure.

(b) Ethyl 6-acetyl-7-hydroxy-4-dimethylamino-8-propyl-quinoline-2-carboxylate

The product of step (a) (2 g; 6.3291 mmole) was dissolved in ethanol and hydrogen chloride was bubbled through the solution. When the heat of soluation subsided, the solution was heated to reflux on a steambath for 2 hours. The mixture was cooled, treated with water and concentrated, followed by basification with NH₃ solution (pH about 6). The solution was extracted into chloroform and this was washed with water, dried and evaporated to give a brown solid (1.6 g, 76%). NMR and mass spectra were consistent with required structure.

(c) Diethyl 6-dimethylamino-4-oxo-10-propyl-4H-pyrano[3,2-g]quinoline-2,8-dicarboxylate A mixture of the product of step (b) (1.6 g; 4.8426 mmole) and diethyl oxalate (5.7 g; 39.041 mmole; 5.3 ml) in dry dimethylformamide (60 ml) was added slowly to a stirring suspension of ether washed sodium hydride (0.29 g; 12.0808 mmole) in dry dimethylformamide (10 ml) under nitrogen. After the addition, the mixture was allowed to stir for 7 hours. The reaction mixture was poured onto ice and was then acidified with dilute hydrochloric acid. The pH of the mixture was adjusted to about 6 before being extracted into chloroform. This was washed with water, dried and evaporated to give a yellow solid. The solid was taken up in ethanolic hydrogen chloride (50 ml) and heated to reflux on the steambath for 3 hours. The solution was cooled, treated with water and then concentrated. The pH of the mixture was adjusted to about 7 and then extracted into chloroform. The extract was washed with water, dried and evaporated, to give a brown solid.

$\delta_{CDCl_3}$: 0.9 (3H,t), 1.4 (6H,t), 1.8 (2H,m) 3.1 (6H,s), 3.5 (2H,m), 4.5 (4H,q), 7.0 (1H,s), 7.35 (1H,s), 8.9 (1H,s).

(d) Disodium 6-dimethylamino-4-oxo-10-propyl-4H-pyrano[3,2-g]quinoline-2,8-dicarboxylate The product of step (c) was hydrolysed by the method of Example 3(g) to afford the sub-title compound.

$\delta_{DMSO}$: 1.0 (3H,t), 1.8 (2H,m), 3.1 (6H,s), 3.5 (2H,t), 7.1 (1H,s), 7.5 (1H,s), 8.8 (1H,s).

EXAMPLE 29

4,6-Dioxo-4H,6H-pyrano[3,2-g]quinazoline-2,8-dicarboxylic acid

(a) Ethyl 6-acetyl-3,4-dihydro-7-hydroxy-4-oxo-quinazoline-2-carboxylate

A mixture of methyl 3-acetyl-4-hydroxy-6-amino benzoate (5 g; 23.9 mmole), ethyl cyano-formate (2.4 g; 24.2 mmole), concentrated hydrochloric acid (2.4 ml) and glacial acetic acid (31.9 ml) was heated on a preheated oilbath (120° C.) for 3 hours. The mixture was cooled to give a white solid. The solid was filtered off and was washed with ice cooled water and then dried in vacuo at 70° C. over P$_2$O$_5$ for 24 hours. NMR and mass spectra were consistent with the required structure.

Elemental analysis: Theoretical: C, 56.52; H, 4.38; N, 10.14%. Found: C, 56.45%; H, 4.52; N, 9.98%.

(b) Diethyl 4,6-dioxo-4H,6H-pyrano[3,2-g]quinazoline-2,8-dicarboxylate

A mixture of diethyl oxalate (4.4 ml) and the product of step (a) (1.1 g; 3.98 mmole) in ethanol (50 ml) was added slowly to freshly prepared sodium ethoxide (0.68 g; 9.99 mmole) in ethanol (80 ml) to give instantly a yellow suspension. After the addition, the mixture was heated to reflux on the steambath for half an hour to give a brown suspension. The mixture was cooled and neutralised with dilute hydrochloric acid to give a bright orange precipitate. This was extraced into chloroform, dried and evaporated to give a bright orange solide. The solid was redissolved in ethanolic hydrogen chloride. The solution was heated to reflux on a steambath for 3 hours. The mixture was cooled and was treated with water. After concentration, this was extracted into chloroform. The organic extract was washed with water, dried and evaporated to give a brown solid (0.95 g, 73%) whose structure was confirmed by NMR and mass spectroscopy.

(c) Disodium 4,6-dioxo-4H,6H-pyrano[3,2-g]quinazoline-2,8-dicarboxylate

The product of step (b) was converted to the sub-title compound by the method of Example 3(g).

$\delta_{DMSO}$: 1.0 (3H,t), 1.6 (2H,m), 3.2 (2H,t), 6.9 (1H,s), 8.5 (1H,s).

EXAMPLE 30

4-Oxo-6-phenylamino-10-propyl-4H-pyrano[3,2-g]quinoline-2,8-dicarboxylic acid

(a) Ethyl 6-acetyl-7-hydroxy-4-phenylamino-8-propyl-quinoline-2-carboxylate Methyl 6-acetyl-4-chloro-7-hydroxy-8-propyl-quinoline-2-carboxylate (1.5 g) was treated with aniline (20 ml) at 175° C. in an autoclave in the presence of p-toluene sulphonic acid (0.1 g) for 72 hours. On cooling the aniline was removed and the residue was heated on a steambath for 12 hours with 70% sulphuric acid. The reaction mixture was poured onto crushed ice and neutralised with ammonia solution to pH 7. Extraction with ethyl acetate followed by drying and evaporation afforded a gum which was taken up in dry ethanol and saturated with hydrogen chloride gas while refluxing for 1 hour. Evaporation of the solvent and trituration with ether afforded the sub-title compound (0.37 g) identified by NMR and mass spectroscopy.

(b) Diethyl 4-oxo-6-phenylamino-10-propyl-4H-pyrano[3,2-g]quinoline-2,8-dicarboxylate The product of step (a) was converted to the sub-title compound by the method of Example 3(f). The structure was confirmed by NMR spectroscopy.

(c) Disodium 4-oxo-6-phenylamino-10-propyl-4H-pyrano[3,2-g]quinoline-2,8-dicarboxylate The product of step (b) was hydrolysed by the method of Example 3(g) to give the title compound identitied by NMR. $\delta_{DMSO}$: 0.95 (3H,t), 1.75 (2H,m), 3.7 (2H,t), 6.95 (1H,s), 7.8 (5H,m), 8.3 (1H,s), 8.75 (1H,s).

EXAMPLE 31

4-Oxo-6-phenylthio-10-propyl-4H-pyrano[3,2-g]quinoline-2,8-dicarboxylic acid

(a) Methyl 6-acetyl-7-hydroxy-4-phenylthio-8-propyl-quinoline-2-carboxylate Phenylthiol (1.87 g) was added to a stirred boiling solution of methyl 6-acetyl-4-chloro-7-hydroxy-8-propyl-quinoline-2-carboxylate (4.97 g) in dry methanol (600 ml) and the solution was boiled for 6 hours. The resulting suspension was cooled and the sub-title compound (2.2 g) filtered off and recrystallised from methanol as yellow needles m.p. 171°-2° C.

(b) Ethyl 8-methoxycarbonyl-4-oxo-6-phenylthio-10-propyl-4H-pyrano[3,2-g]quinoline-2-carboxylate A solution of the product of step (a) (4.0 g) and diethyloxalate (13.0 g) in dry dimethylformamide (275 ml) was slowly added to a stirred suspension of ether washed sodium hydride (50% dispersion in oil, 2.1 g) in dry dimethylformamide (225 ml) under an atmosphere of nitrogen. The resulting suspension was stirred for 1 week then poured into water (1000 ml). The solution formed was acidified with glacial acetic acid, made saline with brine, extracted with ethyl acetate (2×500 ml), washed with water, dried and evaporated to give a brown oil. This oil was dissolved in dry dioxan and dry hydrogen chloride gas was bubbled through it for 15 minutes. The solution was then poured into water, extracted with ethyl acetate (2×300 ml), dried and evaporated to give a yellow brown solid which gave the sub-title compound (1.5 g) after chromatography (SiO$_2$/3:2 40°–60° petroleum ether/ether) as yellow crystals.

The preparation was confirmed by NMR spectroscopy and mass spectroscopy.

(c) Disodium 4-oxo-6-phenylthio-10-propyl-4H-pyrano[3,2-g]quinoline-2,8-dicarboxylate The product of step (b) was hydrolysed by the method of Example 3(g) to give the title compound as a cream solid characterised by NMR spectroscopy.

$\delta_{DMSOd6}$ 1.0 (3H,t), 1.82 (2H,m), 3.7 (2H,t), 7.05 (1M,s) 7.6 (5H,m), 8.4 (1H,s), 8.9 (1H,s).

EXAMPLE 32

Disodium 6-ureido-4-oxo-10-propyl-4H-pyrano[3,2-g]quinoline-2,8-dicarboxylate (a) 6-ureido-4-oxo-10-propyl-4H-pyrano[3,2-g]quinoline-2,8-dicarboxylic acid Diethyl 6-chloro-4-oxo-10-propyl-4H-pyrano[3,2-g]quinoline-2,8-dicarboxylate (1 g) and urea (50 g) were fused together at 175° C. for 6 hours. The solid after cooling was added to 70% sulphuric acid (200 ml) and heated on a steambath for 8 hours. The mixture was poured into ice-water (2 liters) and the precipitate was collected and washed well with water to afford the sub-title compound (0.15 g): identified by NMR spectroscopy.

(b) Disodium 6-ureido-4-oxo-10-propyl-4H-pyrano[3,2-g]quinoline-2,8-dicarboxylate The product of step (a) was converted to the title compound by the method of Example 2(c).

NMR$\delta_{DMSO}$: 0.9 (3H,t), 1.7 (2H,m), 3.6 (2H,t), 6.9 (1H,s), 8.3 (1H,s), 9.0 (1H,s), 11.1 (2H,br).

EXAMPLE 33

6-Chloro-4-oxo-10-propyl-8-tetrazolyl-4H-pyran[3,2-g]quinoline-2-carboxylic acid disodium salt (a) 6-Acetyl-4-chloro-7-hydroxy-8-propylquinoline-2-carboxamide Methyl 6-acetyl-4-chloro-7-hydroxy-8-propylquinoline-2-carboxylate (2 g) was treated with ammonia saturated methanol in an autoclave at 100° C. for 24 hours. Removal of solvent afforded a solid which was boiled with 2 N HCl (100 ml) for 10 minutes, then cooled, and the precipitate was collected and identified as the sub-title compound by NMR.

(b) Ethyl 8-carbamoyl-6-chloro-4-oxo-10-propyl-4H-pyrano[3,2-g]quinoline-2-carboxylate The product of step (a) was converted to the sub-title compound by the method of Example 5 and the structure was confirmed by NMR evidence.

(c) 6-Chloro-4-oxo-10-propyl-8-tetrazolyl-4H-pyrano[3,2-g]quinoline-2-carboxylic acid The product of step (b) (0.5 g) was heated in phosphoryl chloride (10 ml) plus dry dimethylformamide (10 ml) on a steam bath for 2 hours, then poured into ice-water. The precipitate was recovered and dried in vacuo, then mixed with sodium azide (2 g), ammonium chloride (5 g) and suspended in dry dimethylformamide at 100° C. for 18 hours.

The mixture was poured into water and the precipitate was collected and identified as the sub-title compound by NMR and mass spectral evidence.

(d) 6-Chloro-4-oxo-10-propyl-8-tetrazolyl-4H-pyrano[3,2-g]quinoline-2-carboxylic acid, disodium salt The product of step (c) was converted by the method of Example 2(c) to the title compound:

NMR$\delta_{DMSO}$: 1.05 (3H,t), 1.75 (2H,n), 3.6 (2Ht), 6.95 (7Hs), 8.2 (7H,s), 8.95 (7H,s).

EXAMPLE 34

6-Ethoxy-4-oxo-10-propyl-4H-pyrano[3,2-g]quinoline-2,8-dicarboxylic acid (a) Diethyl 6-ethoxy-4-oxo-10-propyl-4H-pyrano[3,2-g]quinoline-2,8-dicarboxylate Methyl 6-acetyl-4-chloro-7-hydroxy-8-propylquinoline-2-carboxylate (1.0 g), and diethyl oxalate (3.7 ml) were added to ether washed sodium hydride (0.65 g) in dry dimethylformamide (20 ml) at room temperature. After stirring for five hours, the whole was poured into ethyl acetate and treated with aqueous acetic acid. The organic layer was washed with water, dried and evaporated. The residue was taken up in saturated ethanolic hydrogen chloride solution (50 ml) and refluxed for 15 minutes. This solution was poured into ethyl acetate and washed with sodium bicarbonate solution. Drying and evaporation afforded a solid which was triturated with light petroleum ether to give a solid (1 g) identified as the sub-title material by NMR and mass spectroscopy.

(b) Disodium 6-ethoxy-4-oxo-10-propyl-4H-pyrano[3,2-g]quinoline-2,8-dicarboxylate 0.1 N Sodium hydroxide solution (56.2 ml) was added dropwise to a refluxing suspension of the product of step (a) above (1.2 g) in methanol (50 ml) over 30 minutes. Refluxing was maintained for 30 minutes after addition was complete, then the mixture was cooled, filtered and all solvent was removed in vacuo. The residue was taken up in water and swamped with acetone. The precipitate was collected and dried to afford 1 g of the title material.

Found: C, 51.25; H, 3.86; N, 3.02%. C$_{19}$H$_{15}$NNa$_2$O$_7$.1.5H$_2$O Requires: C, 51.5; H, 3.73; N, 3.16%.

EXAMPLE 35

6-Chloro-4-oxo-10-propyl-4H-pyrano[3,2-g]quinoline-2,8-dicarboxylic acid (a) 6-Chloro-4-oxo-10-propyl-4H-pyrano-[3,2-g]quinoline-2,8-dicarbonyl chloride (1.31 g) was dissolved in dichloromethane (50 ml), and added dropwise to water (100 ml), at 5° C., with vigorous agitation. When the addition was complete, stirring was continued for an hour. The dichloromethane was removed by distillation in vacuo, and the title compound (1.1 g) collected by filtration, mp 340°.

(b) 6-Chloro-8-formyl-4-oxo-10-propyl-4H-pyrano[3,2-g]quinoline-2-carboxylic acid (0.23 g) in acetone (20 ml) was treated with Jones reagent (0.8 ml), left 20 min. at 0°, then diluted with saturated aqueous sodium chloride, and extracted with 10% sodium bicarbonate. Acidification with 2 N-hydrochloric acid gave the title compound, (200 mg), mp 340° C.

(c) (2-Carboxy-4-chloro-8-propyl-6-quinolyloxy)-butenedioic acid (0.45 g) was dissolved in anhydrous chlorosulphonic acid (3 ml) at 0° C., and allowed to warm to room temperature over 3 hours. The reaction mixture was then poured dropwise into ice/water (200 ml), and filtered. Recrystallisation of the buff powder obtained from ethyl acetate gave the title compound (0.15 g), mp 336°–338°.

EXAMPLE 36

Ethyl 6-chloro-8-methoxycarbonyl-4-oxo-10-propyl-4H-pyrano[3,2-g]quinoline-2-carboxylate Dimethyl (2-ethoxycarbonyl-8-propyl-4-oxo-4H-1-benzopyran-7-ylamino)trans-butenoate (4.17 g) was dissolved in anhydrous dichloromethane (40 ml) and freshly distilled, HCl-free phosphoryl chloride (1.5 ml) added. The solution was refluxed for one hour, to give on cooling, the title compound (1.4 g) as a pale yellow solid, mp 184°–186° C.

EXAMPLE 37

Diethyl 6-ethoxy-4-oxo-10-propyl-4H-pyrano[3,2-g]quinoline-2,8-dicarboxylate

Ethyl 6-chloro-8-methoxycarbonyl-4-oxo-10-propyl-4H-pyrano[3,2-g]quinoline-2-carboxylate (4.0 g) was suspended in ethanol (200 ml), and HCl gas bubbled through, to maintain reflux. After 30 minutes, gassing was stopped, and the whole refluxed for 2 hours. Ethanol was then removed by distillation in vacuo, and the resulting oil chromatographed, to give the title compound (1.2 g), from ethanol, mp 190°–192° C.

EXAMPLE 38

Ethyl 6-chloro-8-methoxycarbonyl-4-oxo-10-propyl-4H-pyrano[3,2-g]quinoline-2-carboxylate Ethyl 6-chloro-2,3-dihydro-8-methoxycarbonyl-4-oxo-10-propyl-4H-pyrano[3,2-g]quinoline-2-carboxylate (0.405 g) was suspended in cymene (10 ml) and refluxed with Pd/C (5%, 0.200 g) for 10 hours. The whole was filtered hot, to remove the catalyst, cooled, poured into petroleum ether (40°–60°, 40 ml), to give a pale buff solid, which was chromatographed of silica, to give the title compound, (0.027 g) mp 174°–176°.

EXAMPLE 39

Diethyl 6-methylamino-4-oxo-10-propyl-4H-pyrano[3,2-g]quinoline-2,8-dicarboxylate Diethyl 6-amino-4-oxo-10-propyl-4H-pyrano[3,2-g]quinoline-2,8-dicarboxylate (0.4 g) was dissolved in dry dimethylformamide (15 ml), and added dropwise with stirring to a suspension of sodium hydride (50%, 0.053 g, washed with dry ether) in dry dimethylformamide (10 ml) under a dry nitrogen atomosphere. After about 30 minutes at ambient temperature a deep red colour had developed, and iodomethane (0.23 ml) was added dropwise and stirring continued at room temperature for a further five hours. The whole ws then poured into water and extracted with chloroform. The organic extracts were combined, dried over magnesium sulphate, evaporated in vacuo, and the resulting oil chromatographed on alumina to give the title compound (0.11 g), mp 235°–237° (from ethanol).

EXAMPLE 40

Ethyl 6-chloro-8-methoxycarbonyl-4-oxo-10-propyl-4H-pyrano[3,2-g]quinoline-2-carboxylate Ethyl 6-chloro-8-methoxycarbonyl-10-propyl-4-thioxo-4H-pyrano[3,2-g]quinoline-2-carboxylate (0.030 g) in acetone (10 ml) containing water (0.2 ml) and methyliodide (0.1 ml) was stirred in the dark at room temperature for 2 days. Concentration of the reaction mixture gave a light buff solid, which was recrystallised from ethanol to give the title compound (0.015 g), mp 176°–179°.

EXAMPLE 41

Diethyl 4-oxo-10-propyl-4H-pyrano[3,2-g]quinoline-2,8-dicarboxylate

Ethyl 6-ethylthio-4-oxo-10-propyl-4H-pyrano[3,2-g]quinoline 2,8-dicarboxylate (2.85 g) was dissolved in ethanol (200 ml), and ethanol washed Raney nickel (30 g wet) added carefully. The mixture was refluxed for 1½ hours, filtered to remove the catalyst, and concentrated, to give on cooling the title compound, (1.76 g) mp 168°–171° C.

EXAMPLE 42

6-Chloro-4-oxo-10-propyl-4H-pyrano[3,2-g]quinoline-2,8-dicarboxylic acid

Cold hypophosphorous acid (50%, 20 ml) was added slowly to a solution of sodium nitrite (3.7 g) in sulphuric acid (100 ml) diluted with water (50 ml), maintaining the temperature from −5° to −10°. The reaction mixture was cooled to −15°, and a cooled solution containing 5-amino-6-chloro-4-oxo-10-propyl-4H-pyrano[3,2-g]quinoline-2,8-dicarboxylic acid (0.753 g) in acetic acid (200 ml), added over two hours maintaining the temperature between −10° and −15°. When the addition was complete, the slurry was stirred for an hour, and the mixture allowed to warm to 5° C. The mixture was stored in a refrigerator overnight, with the evolution of nitrogen and oxides of nitrogen. Filtration of the reaction mixture, and recrystallisation from ethyl acetate, gave 0.43 g of the title compound, mp 338°–340° C.

EXAMPLE 43

6-Methyl-4-oxo-10-propyl-4H-pyrano[3,2-g]quinoline-2,8-dicarboxylic acid 6,7-Dihydro-6-methyl-4-oxo-10-propyl-4H-pyrano[3,2-g]quinoline-2,8-dicarboxylic acid (1.5 g) was heated with sulphur (5 g) to 150° C. with vigorous agitation. After 48 hours the mixture was extracted into saturated sodium bicarbonate solution. Acidification afforded a precipitate (0.12 g) identified as the title compound by NMR and ms.

EXAMPLE A

Clinical evaluation of the compounds was carried out using the antigen inhalation provocation test described below:

The human volunteer selected for test purposes suffered from specific allergic asthma. In this subject an asthma attack normally followed the inhalation of an antigen to which he was specifically sensitive. The degree of asthma provoked by this method can be measured by repeated examination of the air way resistance.

A suitably designed spirometer was used to measure the forced expiratory volume at one second ($F\,E\,V_{1.0}$) hence the changes in air way resistance. The antiallergic activity of a compound is estimated from the difference between the maximum percent $F\,E\,V_{1.0}$ reduction following control and test provocations after drug administration conducted under identical experimental conditions.

The results of the tests are expressed as percent protection according to the formula:

Percent protection =

$$100 \times \frac{\text{av max percent } F\,E\,V_{1.0} \text{ full control shock} - \text{max percent } F\,E\,V_{1.0} \text{ full test shock}}{\text{av max percent } F\,E\,V_{1.0} \text{ full control shock}}$$

The exemplified compounds and particularly the compound of Example 1 (Compound A) produce very considerable protection in the above test.

EXAMPLE B

Compound A was without effect on the blood pressure, heart rate and cardiac output of anaesthatised cats. Compound A did not alter the cardiovascular response to isoprenaline in the cat and rat and is not therefore contra-indicated for use with beta agonist bronchodilators. Compound A also does not produce revulsion when rats are permitted to choose between a food source containing it and a corresponding food source which does not.

The sub-cutaneous $LD_{50}$ of compound A in mice and rats is greater than 2000 mg/kg.

EXAMPLE C

Pharmaceutical Formulations (a) Topical

|  |  | % w/w |
|---|---|---|
| 1. | Oil in water cream | |
|  | Arlacel 165 | 10 |
|  | White soft paraffin | 10 |
|  | Isopropyl myristate | 5 |
|  | Stearic acid | 5 |
|  | Sorbitol solution | 5 |
|  | Compound A | 0.5 |
|  | Preservative | q.s. e.g. 0.2% |
|  | Distilled water | to 100 |
| 2. | Gel | |
|  | Compound A | 1.0% w/w |
|  | Carbomer BP | 2.5 |
|  | Propylene glycol | 28.0 |
|  | Sodium hydroxide | 0.45 |
|  | Distilled water | to 100 |

This composition may be packaged in an internally lacquered aluminium tube fitted with a lined screw cap and folded and crimped at one end.

(b) Rectal

|  |  | |
|---|---|---|
| 3. | Suppository | |
|  | Compound A | 10% w/w |
|  | 'Macrogol' 4000 | 30 |
|  | 'Macrogol' 6000 | 43 |
|  | Distilled water | to 100 |

This composition may be packaged in a plastic strip pack.

(c) Tablets/capsules

|  |  | mg/tablet |
|---|---|---|
| (i) | Compound A (150 micron) | 20 |
|  | Microcrystalline cellulose BPC | 175 |
|  | Sodiumcarboxymethylcellulose | 1 |
|  | Polyvinylpyrrolidone | 2 |
|  | Magnesium stearate | 1.2 |
|  | Colloidal silica | 0.8 |
|  |  | 200.0 |

The finely ground drug is dry mixed with the excipients (excluding magnesium stearate) for 20 minutes, the magnesium stearate added, then mixing continued for a further 5 minutes. The final mixture is then compressed on 8.5 mm diameter normal concave punches to a diametral crushing of 5–7 kp Schleuniger.

|  |  | mg/capsule |
|---|---|---|
| (ii) | Compound A (150 micron) | 20 |
|  | Lactose B.P. | 98 |
|  | Sodiumcarboxymethylcellulose | 1 |
|  | Magnesium stearate | 0.5 |
|  | Colloidal silica | 0.5 |
|  |  | 120.0 |

The powders are dry mixed in a similar manner as for (i) above, and the final mixture filled on a capsule machine into Size 2 hard gelatin capsule shells.

The tablets or capsules may be loose filled into internally lacquered aluminium cans or packed in a polyvinylidene chloride/aluminium foil blister overwrapped with an aluminium foil.

|  |  | mg/tablet |
|---|---|---|
| (iii) | Compound A (90 micron) | 200 |
|  | Sodium Bicarbonate BP | 80 |
|  | Maize starch as disintegrant | 32 |
|  | Maize starch as binder | 8–16 |
|  | Lactose BP | 70–78 |
|  | Magnesium stearate | 2 |
|  |  | 400.0 |

The drug, lactose, sodium bicarbonate and starch disintegrant are mixed and this powder then moistened with a 10% w/w aqueous mucilage of the starch binder (about 30 g per 100 g of dry powder). The wet mass is passed through a 1000 micrometer screen and dried at 60° C. for 3 hours. The dry product is passed through a 710 micrometer screen and blended with the magnesium stearate before compressing on a tablet machine to a diametral crushing strength of 6–8 kp Schleuniger.

(d) Lozenges

|  | mg/lozenge |
|---|---|
| Compound A (micronized) | 10 |
| Sugar, pulverised BP (196 g) | 765 |
| Stearic acid BPC | |
| intragranule | 6.00 |
| extragranule | 5.40 |
| Menthol BP | 0.62 |
| Eucalyptus Oil BP | 1.80 |
| Oil of Lemon, Terpeneless BPC | 0.18 |
| Granulating Solution: | |
| Liquid Glucose BPC | 5.50 |
| Gelatin BP | 5.50 |
| | 800.00 |

The drug, sugar and intragranule stearic acid are mixed, then moistened with an aqueous solution containing 10% w/w liquid glucose, 10% w/w gelatin. The moistened mass is passed through a 1000 micrometer screen, dried at 60° C. for 3 hours and re-passed through a 1000 micrometer screen. The menthol is dissolved in a mixture of eucalyptus oil and lemon oil and mixed for 10 minutes with about 10% of the dry granules. These mixed granules are added with the extragranule stearic acid to the remaining granules and mixed for a further 5 minutes. The product is then compressed on 12 mm diameter flat-faced, bevelled edge punches in a tablet machine to a diametral crushing strength of 7-9 kp Schleuniger.

The lozenges may be roll wrapped with an aluminium foil laminate and packed into aluminium tubes.

(e) Brushable paste

|  | % w/w |
|---|---|
| Compound A | 4 |
| Sodium Carboxymethylcellulose | 1.5 |
| Glycerol | 25 |
| Nipastat | 0.1 |
| Propylene glycol | 0.4 |
| Sodium saccharin | 0.1 |
| Water | 25.2 |
| Sodium lauryl sulphate | 2 |
| Dicalcium phosphate dihydrate | 41 |
| Flavour | 0.7 |

The Nipastat is dispersed in the propylene glycol and heated to 50° C. with the glycerol. The sodium carboxymethylcellulose is added with rapid stirring to aid dispersion, and the water containing the dissolved drug then added while slowly stirring. Stirring is continued for 20 minutes until the components are fully dispersed, maintaining the vessel at 50° C. throughout, and a vacuum then applied to deaerate the dispersion while stirring is continued for a further 10 minutes. The dicalcium phosphate dihydrate is mixed in under vacuum, and finally, sodium lauryl sulphate and flavour are similarly mixed in before cooling the contents to 25°-30° C. before filling the paste into, e.g. epoxy lacquered aluminium tubes or other containers.

(f) Intravenous or eye drop formulation

| Compound A | 0.50 g |
|---|---|
| Sodium chloride | 0.84 g |
| Water for injection (low metals) | to 100 ml |
| Sterilisation is achieved by filtration. | |

(g) instramuscular Formulation:

| Compound A | 0.025 g |
|---|---|
| Propylene glycol | 3.0 ml |
| Water for Injection (low Metals) | to 5.0 ml |

Preparation is as for the i.v. formulation and may be packaged in neutral glass ampoules or multidose vials.

(h) Inhalation powder formulation

| (a) lung (for inhalation) | Weight per capsule | % w/w |
|---|---|---|
| Compound A (micronised) | 5 mg* | 12.5* |
| Classified lactose (substantially 30 to 80 microns) | q.s. ad 40 mg | q.s. ad 100.0 |

*As anhydrous material

| (b) nose (for insufflation) | Weight per capsule | % w/w |
|---|---|---|
| Compound A (micronised) | 2.5 mg* | 12.5* |
| Classified lactose (substantially 30 to 80 microns) | q.s. ad 20 mg | q.s. ad 100.0 |

*As anhydrous material

Use one capsule for each nostril

METHOD:
Place half of the lactose in a suitable mixer and add the micronised drug. Add the remaining lactose and mix until homogeneous. Fill into No. 2 hard gelatin capsules using either automatic or semi-automatic filling machines.

(i) Aerosol formulation (cold-fill)

|  | % w/w |
|---|---|
| Compound A (micronised) | 2.8339* |
| Sorbitan trioleated | 0.5047 |
| Propellent 114 | 38.6446 |
| Propellent 12 | 57.9668 |

*As anhydrous material

METHOD:
Cool the propellent 12 to −55° C. and disperse the sorbitan trioleate in it using a high-shear mixer. Disperse the drug in this mix and finally add the propellant 114, cooled to −55° C. Fill into suitable cans while still cold, fit a metering valve and crimp.

(j) Aerosol formulation (concentrate/pressure fill)

| (i) | Concentrate | % w/w |
|---|---|---|
| | Compound A (micronised) | 6.9009 |
| | Dioctyl Sodium Sulphosuccinate | 0.2393 |
| | Propellent 114 | 92.8598 |

METHOD:
Cool the propellent 114 to 0° C. and dissolve in it the dioctyl sodium sulphosuccinate. Add the micronised drug and disperse using a high-shear mixer. Maintain at 0° C.

| (ii) | Cans | Weight per can |
|---|---|---|
| | Concentrate | 6.81 g |
| | Propellent 12 | 9.49 g |

METHOD:

Dispense the concentrate at 0° C. into the cans and seal each by crimping on a suitable metering valve. Pressure fill the required quantity of propellent 12 into each can.

We claim:

1. A compound selected from the group having the formulas

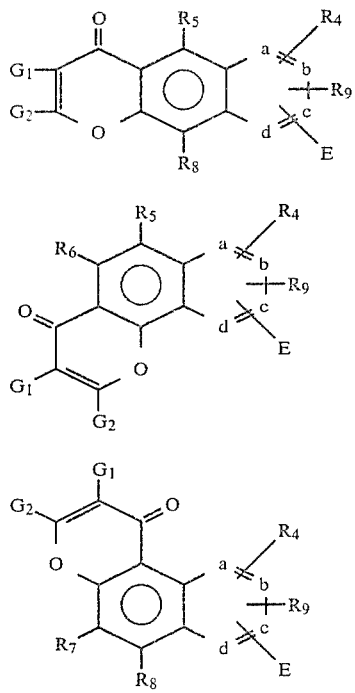

wherein
one of the atoms a and d is nitrogen and the other is carbon, and b and c are carbon,
$R_4$, $R_5$, $R_6$, $R_7$, $R_8$, and $R_9$, which may be the same or different, each represent hydrogen, alkyl, halogen, alkenyl, $-NO_2$, $-NR_1R_2$, $-OR_3$, $-S(O)_nR_3$; or alkyl substituted by hydroxy, amino, alkoxy or carbonyl oxygen,
n is 0, 1 or 2,
$R_1$ and $R_2$, which may be the same or different, each represent hydrogen, alkyl, $-CONHR_3$, phenyl or phenyl substituted by alkyl or halogen, or $R_1$ and $R_2$ together with the nitrogen atom to which they are attached form a morpholine, piperidine or pyrrolidine ring,
$R_3$ represents hydrogen, alkyl, alkenyl or phenyl,
one of $G_1$ and $G_2$ is hydrogen and the other is a group E,
each E, which may be the same or different, is $-COOH$, a 5-tetrazolyl group, or a group having the formula

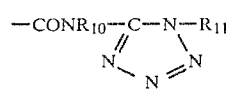

$R_{10}$ and $R_{11}$ are the same or different and are hydrogen, alkyl, alkenyl, phenylalkyl, alkanoyl, or alkoxy carbonyl, and $R_{10}$ is hydrogen when $R_{11}$ is hydrogen, $R_1$, $R_2$, $R_3$, $R_4$, $R_5$, $R_6$, $R_7$, $R_8$, $R_9$, $R_{10}$ and $R_{11}$, when they contain carbon, each containing up to 8 carbon atoms,
provided that when (i) either a or d is a carbon atom, (ii) E is in a position ortho to the N atom and is $-COOH$, a 5-tetrazolyl group or an unsubstituted (N-tetrazol-5-yl)carboxamido group, (iii) $R_9$ is hydrogen, (iv) $G_1$ is hydrogen and $G_2$ is a group E, and (v) $R_5$, $R_6$, $R_7$ and $R_8$ are selected from hydrogen, hydroxy, alkyl, halogen, alkenyl, alkoxy or $-NR_1R_2$, then $R_4$ is not an $-OH$ group para to the N atom,
and pharmaceutically acceptable salts, and when E is $-COOH$, pharmaceutically acceptable lower alkyl esters, 2-(diethylamino)esters and lower alkanoyl-lower alkyl esters, and pharmaceutically acceptable unsubstituted or mono- or di-phenyl or $C_1$ to $C_6$ alkyl amides, thereof.

2. A compound according to claim 1, wherein each of $R_1$, $R_2$, $R_3$, $R_4$, $R_5$, $R_6$, $R_7$, $R_8$, $R_9$, $R_{10}$, and $R_{11}$, when it contains carbon, has up to 4 carbon atoms.

3. A compound according to claim 1, wherein $R_4$, $R_5$, $R_6$, $R_7$, $R_8$ and $R_9$ are selected from hydrogen, methoxy, propyl, allyl, methyl, ethyl chlorine, bromine, amino, methylamino, thioethyl, propenyloxy, allyl, phenoxy, ureido and hydroxy.

4. A compound according to claim 1, wherein $R_3$ is hydrogen or alkyl.

5. A compound according to claim 1, wherein $G_1$ is hydrogen and $G_2$ is E.

6. A compound according to claim 1, wherein $R_5$ is hydrogen and $R_8$ is alkyl.

7. A compound according to claim 6, wherein $R_8$ is propyl.

8. A compound according to claim 1, wherein d is nitrogen.

9. A compound according to claim 1, wherein an E group is in a position adjacent to a ring N-atom.

10. A compound according to claim 1, wherein both E groups are the same and are $-COOH$.

11. A compound according to claim 1, wherein $R_9$ is hydrogen.

12. A compound according to claim 1, wherein $R_4$ is para to an N-atom at position d.

13. A compound according to claim 1, wherein $R_4$ is hydrogen, halogen, $-OR_3$, $-SR_3$ or $-NR_1R_2$.

14. A compound according to claim 1, wherein $R_4$ is other than $-OH$.

15. A compound according to claim 1, wherein $R_4$ is chlorine.

16. A compound in accordance with claim 1 having the formula

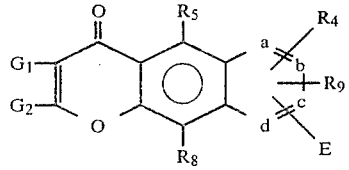

and pharmaceutically acceptable salts, and when E is $-COOH$, lower alkyl esters thereof.

17. A compound according to claim 16, which is 6 chloro-4-oxo-10-propyl-4H-pyrano[3,2-g]quinoline-2,8-dicarboxylic acid.

18. A compound according to claim 16, which is disodium 6-chloro-4-oxo-10-propyl-4H-pyrano[3,2-g]quinoline-2,8-dicarboxylate.

19. A compound according to claim 16, and selected from 6-methoxy-4-oxo-10-propyl-4H-pyrano[3,2-g]quinoline-2,8-dicarboxylic acid,
6-ethylthio-4-oxo-10-propyl-4H-pyrano[3,2-g]quinoline-2,8-dicarboxylic acid,
6-bromo-4-oxo-10-propyl-4H-pyrano[3,2-g]quinoline-2,8-dicarboxylic acid,
6-methyl-4-oxo-10-propyl-4H-pyrano[3,2-g]quinoline-2,8-dicarboxylic acid,
4,6-dioxo-10-propyl-4H,6H-pyrano[3,2-g]quinoline-3,8-dicarboxylic acid,
4-oxo-6-(prop-2-enyloxy)-10-propyl-4H-pyrano[3,2-g]quinoline-2,8-dicarboxylic acid,
4,6-dioxo-7-(2-propenyl)-10-propyl-4H,6H-pyrano[3,2-g]quinoline-2,8-dicarboxylic acid,
4,6-dioxo-7,10-dipropyl-4H,6H-pyrano[3,2-g]quinoline-2,8-dicarboxylic acid,
6-chloro-4-oxo-7,10-dipropyl-4H-pyrano[3,2-g]quinoline-2,8-dicarboxylic acid,
7-chloro-5-methoxy-4-oxo-4H-pyrano[3,2-g]quinoline-2,9-dicarboxylic acid,
6-chloro-4-oxo-10-(prop-2-enyl)-4H-pyrano[3,2-g]quinoline-2,8-dicarboxylic acid,
6-ethylsulphinyl-4-oxo-10-propyl-4H-pyrano[3,2-g]quinoline-2,8-dicarboxylic acid,
6-ethylsulphonyl-4-oxo-10-propyl-4H-pyrano[3,2-g]quinoline-2,8-dicarboxylic acid,
4-oxo-10-propyl-4H-pyrano[3,2-g]quinoline-2,8-dicarboxylic acid,
4-oxo-6-phenoxy-10-propyl-4H-pyrano[3,2-g]quinoline-2,8-dicarboxylic acid,
4-oxo-10-propyl-6-(1-pyrrolidino)-4H-pyrano[3,2-g]quinoline-2,8-dicarboxylic acid,
N,N'-di-5-tetrazolyl-6-chloro-4-oxo-10-propyl-4H-[3,2-g]pyranoquinoline-2,8-dicarboxamide,
6-chloro-10-methyl-4-oxo-4H-pyrano[3,2-g]quinoline-2,8-dicarboxylic acid,
6-ethylamino-4-oxo-10-propyl-4H-pyrano[3,2-g]quinoline-2,8-dicarboxylic acid,
6-dimethylamino-4-oxo-10-propyl-4H-pyrano[3,2-g]quinoline-2,8-dicarboxylic acid,
4-oxo-6-phenylamino-10-propyl-4H-pyrano[3,2-g]quinoline-2,8-dicarboxylic acid,
4-oxo-6-phenylthio-10-propyl-4H-pyrano[3,2-g]quinoline-2,8-dicarboxylic acid,
6-ureido-4-oxo-10-propyl-4H-pyrano[3,2-g]quinoline-2,8-dicarboxylic acid,
6-chloro-4-oxo-10-propyl-8-tetrazolyl-4H-pyran[3,2-g]quinoline-2-carboxylic acid,
6-ethoxy-4-oxo-10-propyl-4H-pyrano[3,2-g]quinoline-2,8-dicarboxylic acid,
and pharmaceutically acceptable salts thereof.

20. A compound according to claim 16, which is 6-methylamino-4-oxo-10-propyl-4H-pyrano[3,2-g]quinoline-2,8-dicarboxylic acid or a pharmaceutically acceptable salt thereof.

21. A compound in accordance with claim 1 having the formula

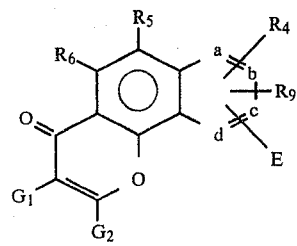

and pharmaceutically acceptable salts, and when E is —COOH, lower alkyl esters thereof.

22. A compound according to claim 21, which is 10-chloro-4-oxo-4H-pyrano[2,3-f]quinoline-2,8-dicarboxylic acid, or a pharmaceutically acceptable salt thereof.

23. A compound in accordance with claim 1, having the formula

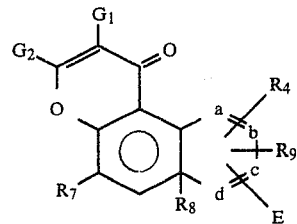

and pharmaceutically acceptable salts, and when E is —COOH, lower alkyl esters thereof.

24. A compound according to claim 23 and selected from 4-chloro-10-oxo-10H-pyrano[2,3-h]quinoline-2,8-dicarboxylic acid,
10-chloro-1-oxo-1H-pyrano[3,2-f]quinoline-3,8-dicarboxylic acid,
and pharmaceutically acceptable salts thereof.

25. A pharmaceutical composition for treatment of a condition involving an antigen-antibody reaction or excess mucous secretion comprising a therapeutically effective amount of a compound according to claim 1, as active ingredient, in combination with a pharmaceutically acceptable inert adjuvant, diluent or carrier.

26. A composition according to claim 25 in a form suitable for inhalation.

27. A composition according to claim 25 comprising from 0.001 to 200 mg of active ingredient in unit dosage form.

28. A method of treatment of a condition involving an antigen-antibody reaction or excess mucous secretion, which comprises administering an effective amount of a compound according to claim 1 to a patient suffering from such a condition.

29. A method according to claim 28, wherein the condition to be treated is asthma.

30. A composition in accordance with claims 25, 26 or 27 wherein said compound is 6-methylamino-4-oxo-10-propyl-4H-pyrano[3,2-g]quinoline-2,8-dicarboxylic acid, or a pharmaceutically acceptable salt thereof.

31. A method in accordance with claims 28 or 29 wherein said compound is 6-methylamino-4-oxo-10-propyl-4H-pyrano[3,2-g]quinoline-2,8-dicarboxylic acid, or a pharmaceutically acceptable salt thereof.

* * * * *